United States Patent [19]
Dupont et al.

[11] Patent Number: 5,985,839
[45] Date of Patent: *Nov. 16, 1999

[54] EXTRACTS OF SHARK CARTILAGE HAVING AN ANTI-ANGIOGENIC ACTIVITY AND AN EFFECT ON TUMOR REGRESSION: PROCESS OF MAKING THEREOF

[75] Inventors: Eric Dupont, St. Nicolas; Paul Brazeau, Montreal; Christian Juneau, Ste. Foy, all of Canada

[73] Assignee: Les Laboratories Aeterna Inc., Quebec, Canada

[*] Notice: This patent is subject to a terminal disclaimer.

[21] Appl. No.: 08/727,300

[22] Filed: Oct. 8, 1996

Related U.S. Application Data

[63] Continuation of application No. 08/384,555, Feb. 3, 1995, Pat. No. 5,618,925, which is a continuation-in-part of application No. 08/234,019, Apr. 28, 1994, abandoned.

[51] Int. Cl.$^6$ .............................. A61K 38/00; C07K 1/00; A21J 1/00
[52] U.S. Cl. ........................... 514/21; 514/828; 514/855; 514/859; 514/863; 514/886; 514/887; 530/400; 530/412; 530/414; 530/415; 530/417; 530/418; 530/427
[58] Field of Search .............................. 514/21, 828, 855, 514/859, 863, 886, 887; 530/400, 412, 414, 415, 417, 418, 427

[56] References Cited

U.S. PATENT DOCUMENTS

| | | | |
|---|---|---|---|
| 3,478,146 | 11/1969 | Balassa | 424/95 |
| 4,042,457 | 8/1977 | Kuettner et al. | 550/356 |
| 4,243,582 | 1/1981 | Spilburg et al. | 530/395 |
| 4,350,682 | 9/1982 | Balassa | 424/64 |
| 4,356,261 | 10/1982 | Kuettner | 435/68 |
| 4,473,551 | 9/1984 | Schinitsky | 424/95 |
| 4,656,137 | 4/1987 | Balassa | 435/267 |
| 4,746,729 | 5/1988 | Kuettner et al. | 530/353 |
| 4,749,522 | 6/1988 | Kamarei | 424/95 |
| 4,822,607 | 4/1989 | Balassa et al. | 424/95 |
| 5,075,112 | 12/1991 | Lane | 424/434 |

FOREIGN PATENT DOCUMENTS

| | | |
|---|---|---|
| WO 94/12510 | 6/1994 | WIPO. |
| WO 95/03036 | 2/1995 | WIPO. |
| WO95/32722 | 12/1995 | WIPO. |

OTHER PUBLICATIONS

Oikawa et al, *Cancer Letters*, vol. 51, pp. 181–186, 1990.
Luer et al, *Abstract of Fed. Proc.*, vol. 45, No. 4, pp. 949, Abstract No. 4624, 1986.
Laue et al, *Methods in Enzynology*, vol. 182, Chapter 43, pp. 566–587, 1990.
Chabot–Fletcher, M. et al. (1994). "Interleukin–8 Production is Regulated by Protein Kinase C in Human Keratinocytes". *The Journal of Investigative Dermatology* 103(4): 509–515.
Folkman, J. and M. Klagsbrun (1987). "Angiogenic Factors". *Science*. 235: 442–446.
Langer, R et al. (1976). "Isolation of a Cartilage Factor That Inhibits Tumor Neovascularisation", *Science*. 193: 70–72.
Lee, A. and R. Langer (1983). "Shark Cartilage Contains Inhibitors of Tumor Angiogenesis". *Science*. 221: 1185–1187.
Luer, C.A. (1986). "Inhibitors of Angiogenesis from Shark Cartilage". Fed. Proc. 45(4): 949, Abstract 4624.
Moses, M.A. and R. Langer (1991). "Inhibitors of Angiogenesis". *Biotechnology* 9:630–634.
Nickoloff, B.J. et al. (1994). "Aberrant Production of Interleukin–8 and Thrombospondin–1 Psoriastic Keratinocytes Mediates Angiogenesis". *Am. J. Pathology* 144(4): 820–828.
Oikawa, T. et al. (1990) "A novel angiogenic inhibitor derived from Japanese shark cartilage (I). Extraction and estimation of inhibitory activities toward tumor and embyronic angiogenesis". *Cancer Letters* 51: 181–186.
Suzuki, F. et al. (1984). "Cartilage–derived Antitumor Factor (CATF): A High Molecular Weight Fraction in Cartilge Extract Inhibits Solid Tumor Growth". *J. of Bone and Mineral Metabolism* 2(3): 3–7.

*Primary Examiner*—Cecilia Tsang
*Assistant Examiner*—Abdel A. Mohamed
*Attorney, Agent, or Firm*—Rick Matos; Akin, Gump, Strauss, Hauer & Feld, L.L.P.

[57] ABSTRACT

The present invention relates to shark cartilage extracts and to a method of producing the same, these extracts having anti-angiogenic properties (reduction of the area of blood vessels observed in vivo on experimentally induced tumors), tumor regressive activity in vivo as well as demonstrating a direct inhibitory effect on tumor cell lines. This process does not involve any denaturing solvent or product and does not involve the use of any enzymes. It consists of obtaining a blend of whole cartilage in an aqueous solution of neutral pH, preferably pure water, this blend being centrifuged and the pellet and supernatant kept for further processing. The pellet is lyophilized and tested for anti-tumor and anti-angiogenic activities in vivo and in vitro, with or without supernatant. The supernatant has been shown to have anti-angiogenic and tumor regressive activities in vivo. The composition of the supernatant has then been investigated by different ways. Fractionation of this supernatant led to the characterization of some of its active components. The fractions were tested for their direct in vitro activity on cancer cell lines. Therefore, it is assumed that the non-fractionated supernatant has such an in vitro activity. Lyophilization substantially destroys the activity of these liquid fractions while no such abolition is observed in the solid extract.

57 Claims, 14 Drawing Sheets

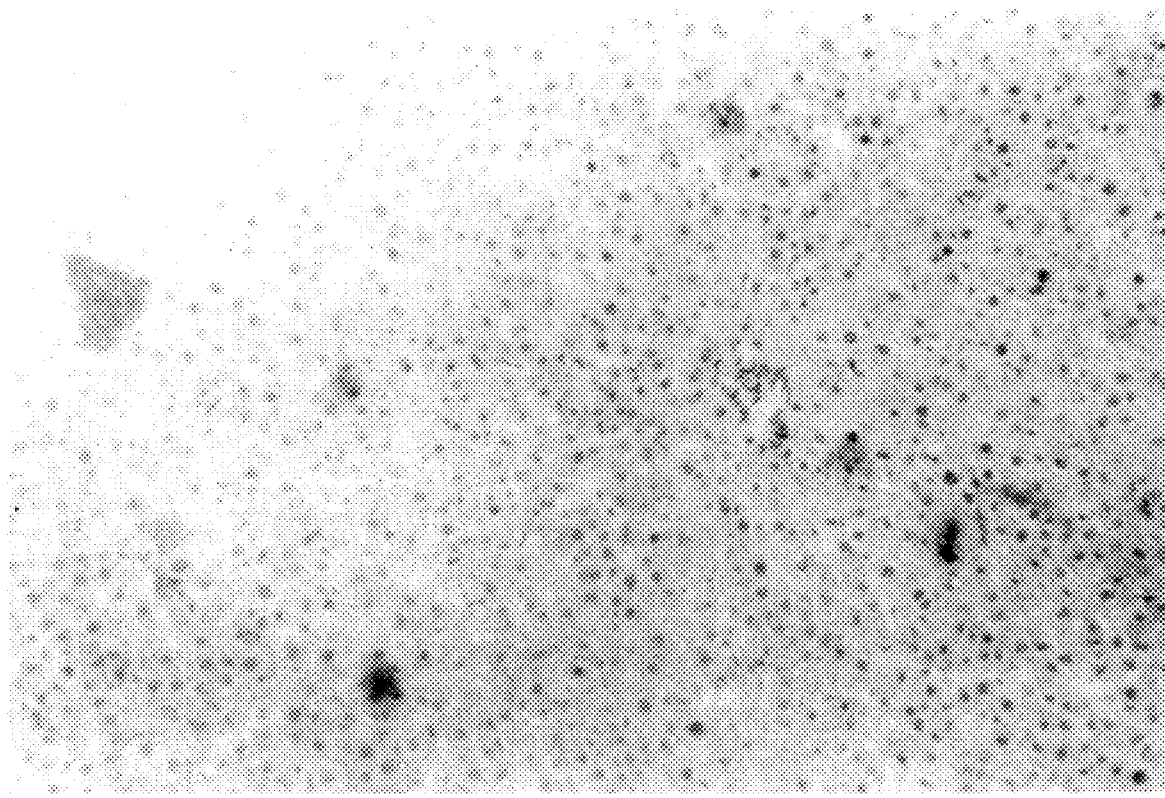
Figure 3a  Liver section from a control animal. The cytoplasm and nuclei of parenchymal cells show a normal appearance. X200.
Each micrograph (magnification: X200) shows a representative section from either a control (vehicle-treated) adult female rat or an adult female rat treated with the highest dose of shark cartilage extracts administered by intragastric tubing.

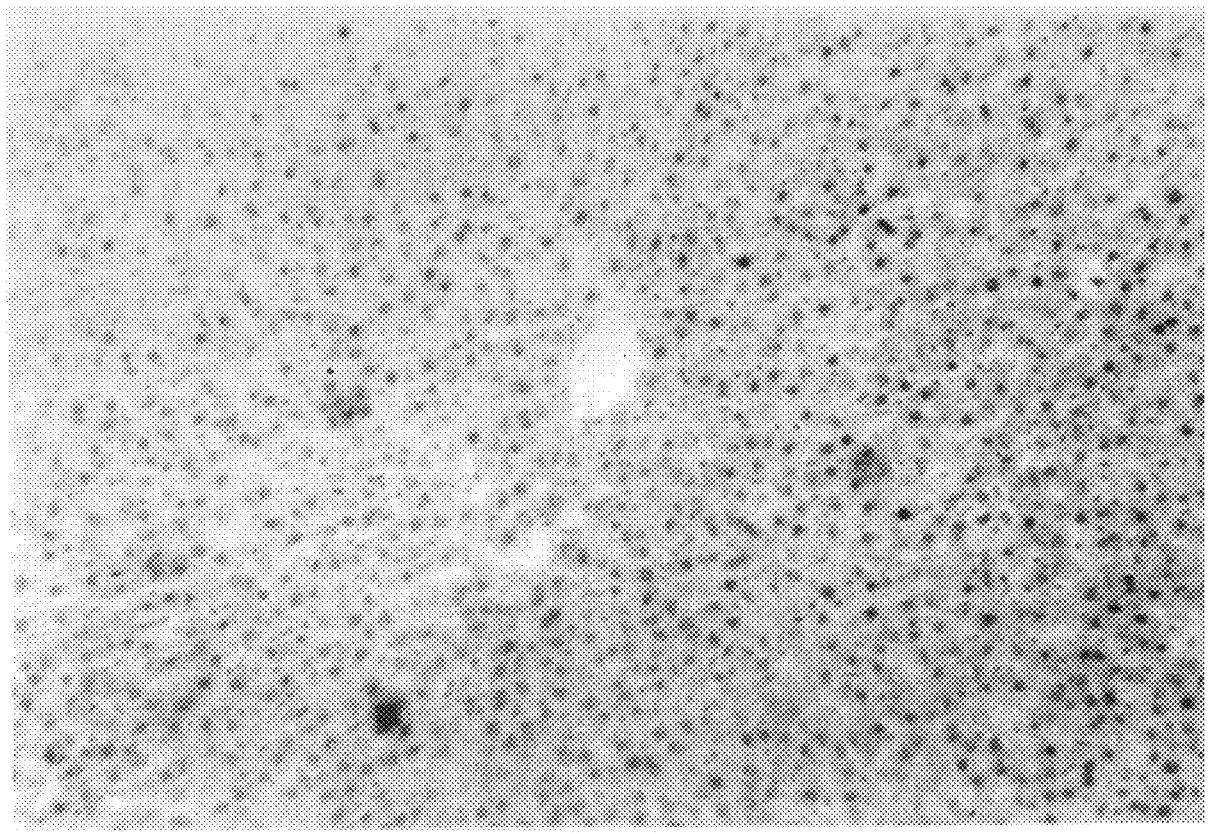
Figure 3b  Liver section from a treated animal. The appearance of the cytoplasm and nuclei is very similar to that observed in the control animal (see Fig. 3a). No degenerative changes can be observed. X200.

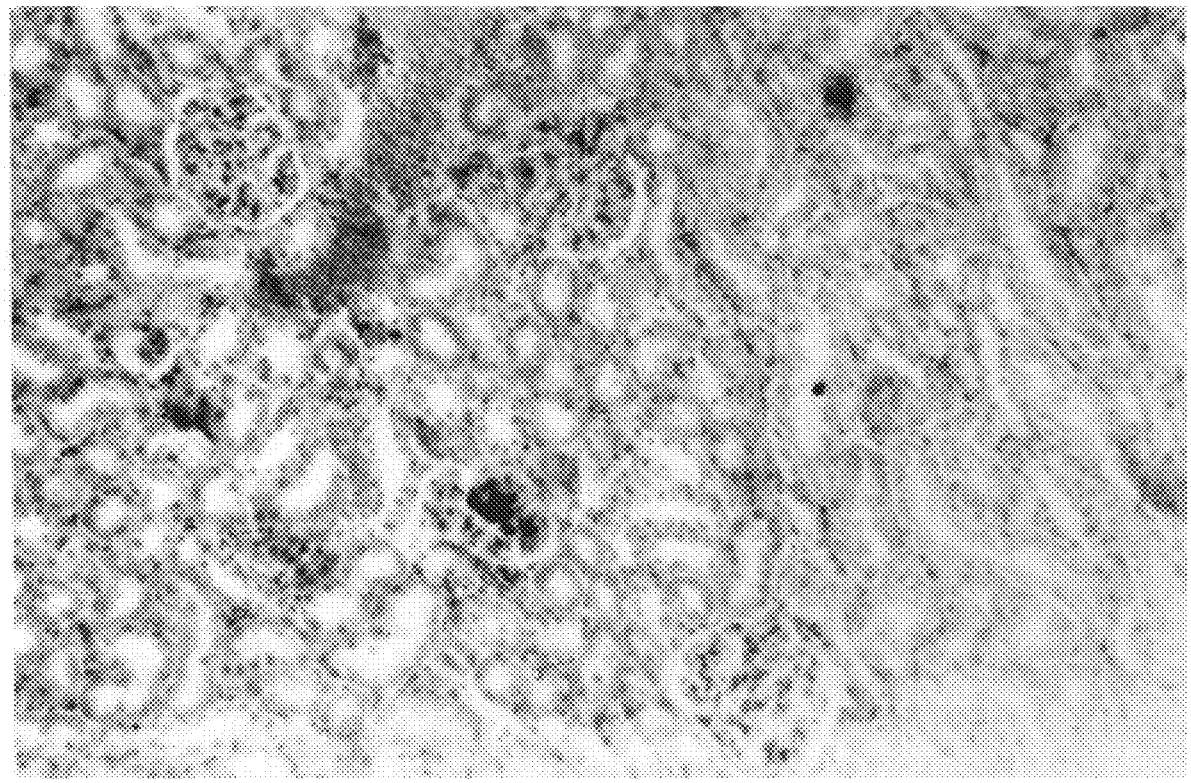
Figure 4a  Control animal. Section through the cortex of a kidney. All the tubular cells appear normal with clear and well delimited cytoplasm. The tubular lumen are empty. X200.

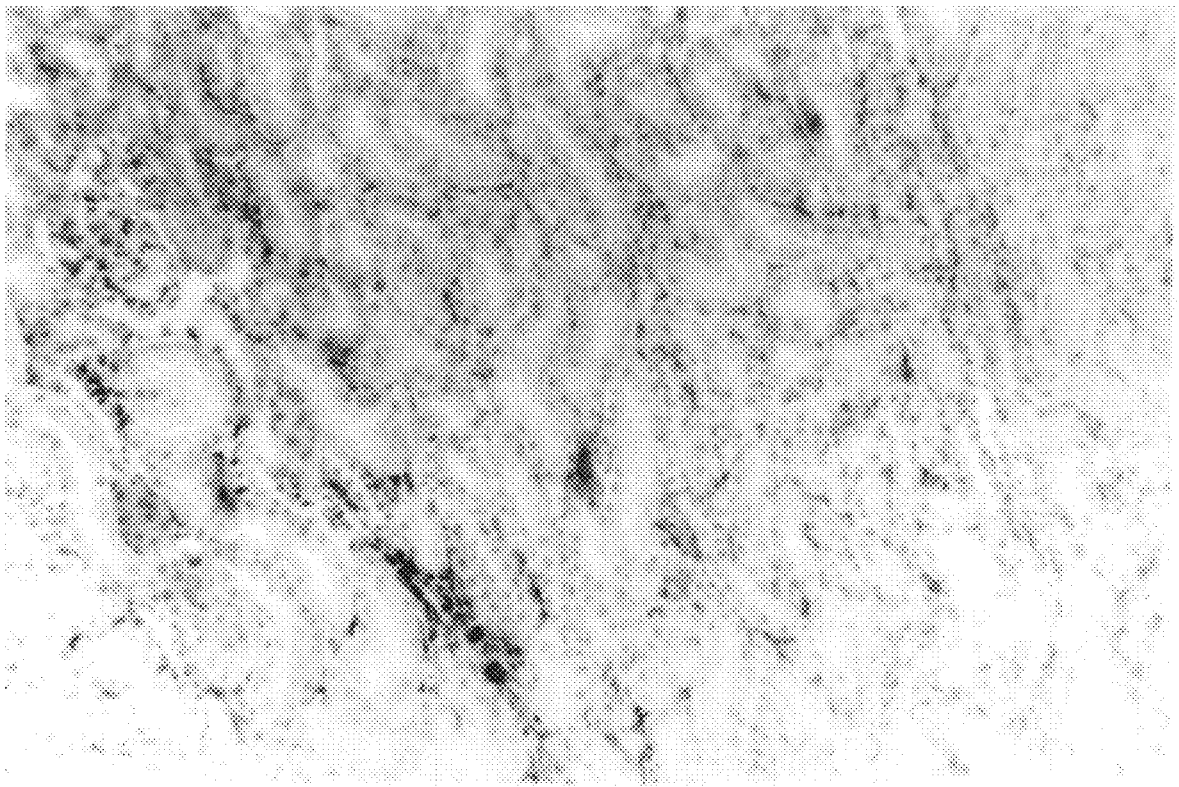
Figure 4b treated animal. Section through the cortex of a kidney. The tubular cells have a normal appearance. There is no desquamated cells in the lumen of the tubules. No signs of toxicity can be detected. X200.

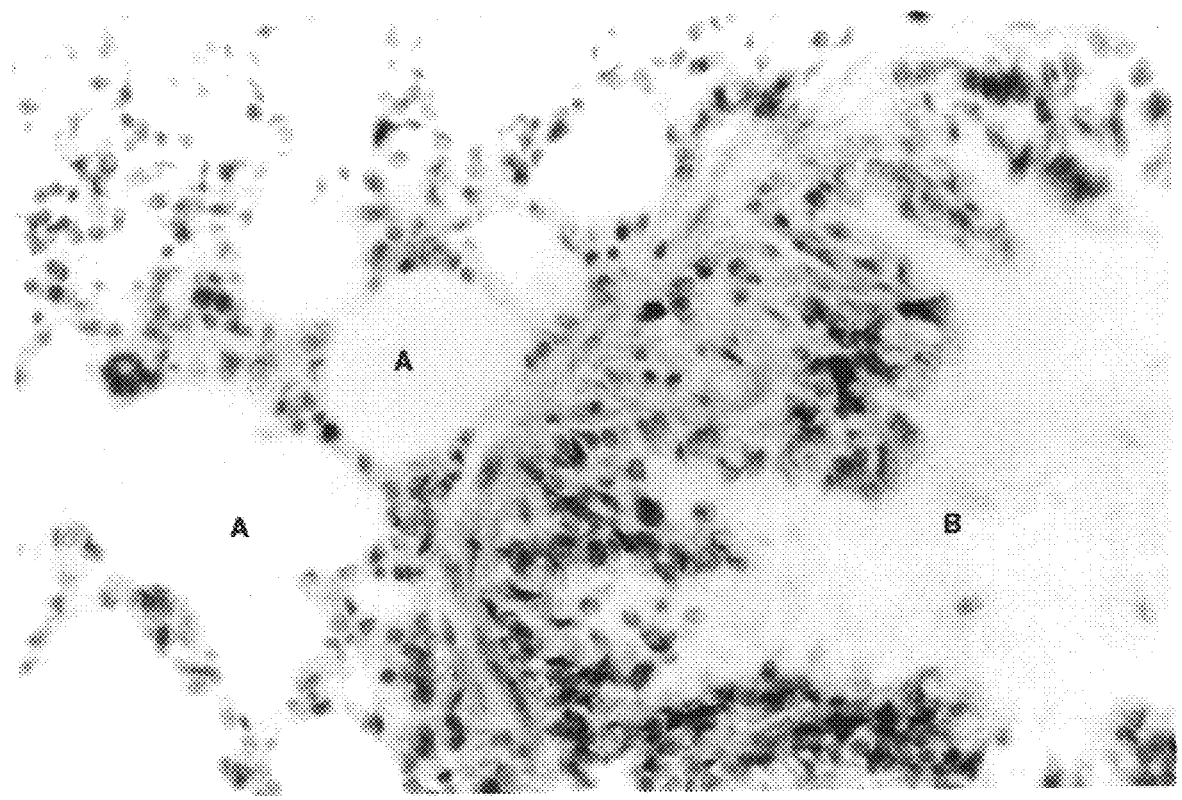
Figure 5a  Control rat. Section through a lung. The wall of a bronchiole (B) as well as of alveoli (A) appear intact with well delimited epithelial cells. X200.

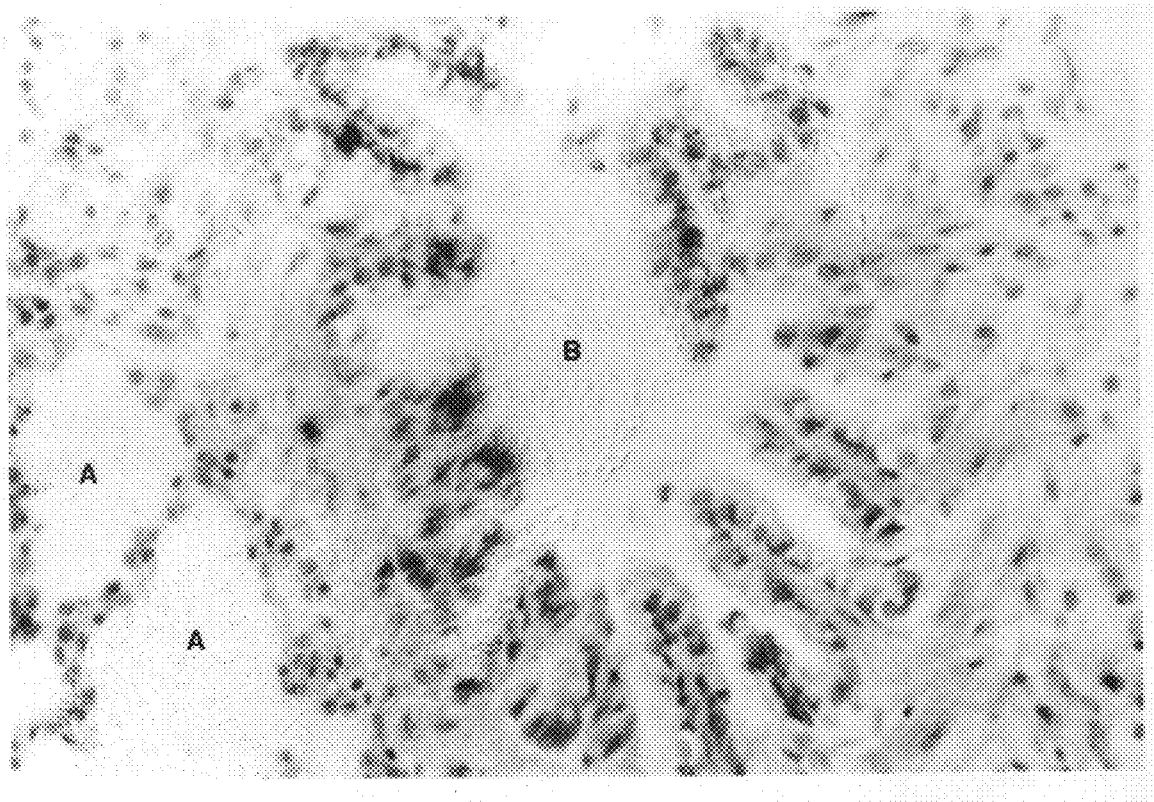
Figure 5b  treated animal. Section through the lung. The cells in the walls of a bronchiole (B) and alveoli (A) have a normal appearance, being very similar to those observed in control animals (Fig. 5a). The lumen are free of any desquamated cells. X200.

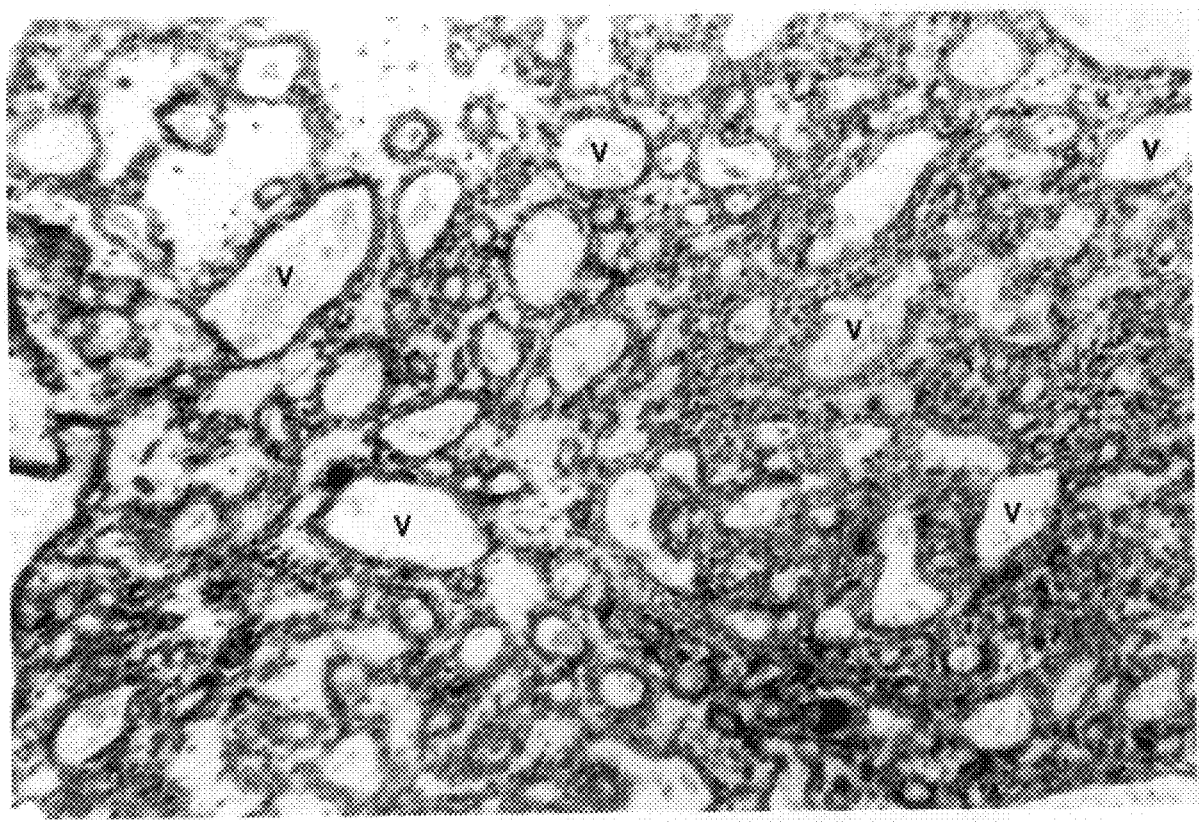
Figure 6a  Control rat. DMBA-induced mammary tumor. Blood vessels are numerous and some of them (V) are large. X120.

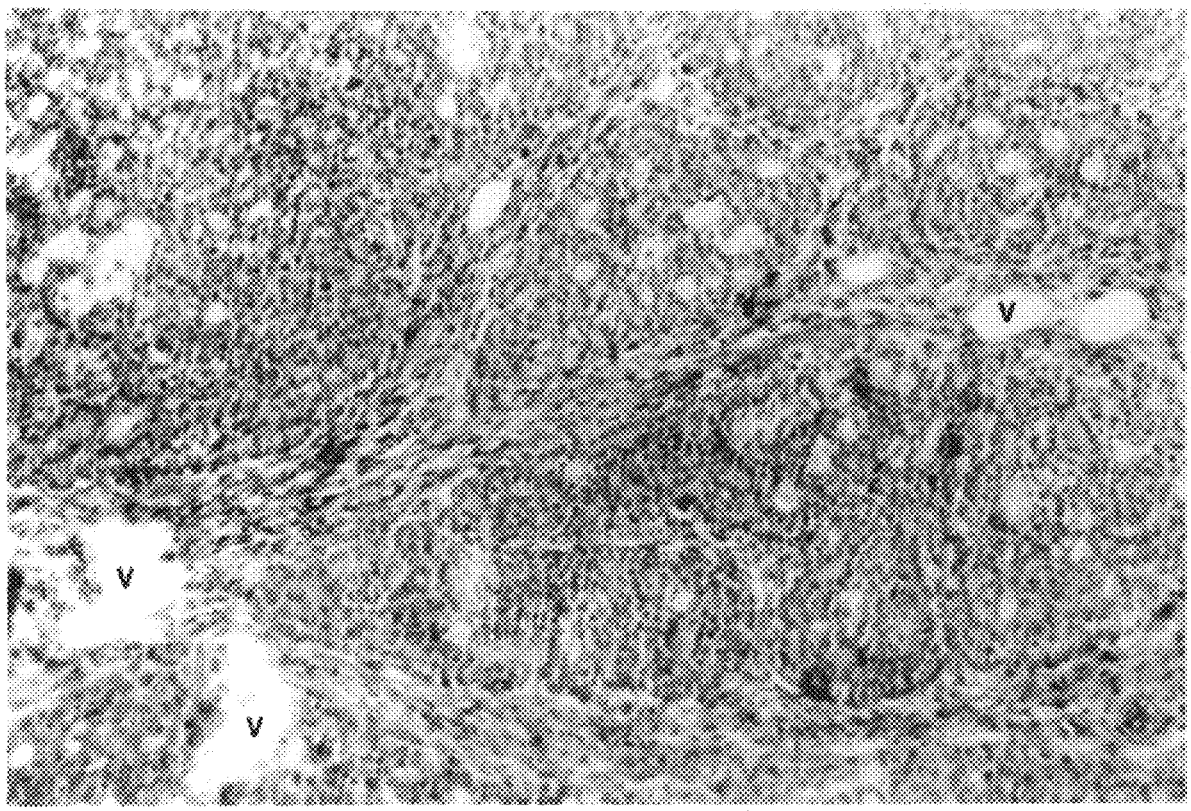
Figure 6b  Treated rat. DMBA-induced mammary tumor. there are major histological changes due to the decrease in the number and size of blood vessels (V). This provides the appearance of a more compact tissue. X120.

Figure 9a) Patient suffering of psoriasis with keratosis before treatment.
Figure 9b) Patient of Figure 9a) after one month of topical application of a formulation containing the liquid cartilage extract.

Figure 10a) Patient suffering of psoriasis without keratosis before treatment.
Figure 10b) Patient of Figure 10a) after three months of topical application of a formulation containing the liquid cartilage extract.

EXTRACTS OF SHARK CARTILAGE HAVING AN ANTI-ANGIOGENIC ACTIVITY AND AN EFFECT ON TUMOR REGRESSION: PROCESS OF MAKING THEREOF

This is a continuation of appln. Ser. No. 08/384,555, filed Feb. 3, 1995, now U.S. Pat. No. 5,618,925; which is a continuation-in-part of appln. Ser. No. 08/234,019, filed Apr. 28, 1994, now abandoned.

BACKGROUND OF THE INVENTION

Cartilage is an avascularized tissue and has been studied as a potential candidate containing anti-angiogenic factors. It is also a tissue which is relatively resistant to tumor development. The tumor associated with cartilage, chondrosarcoma, is the least vascularized of solid tumors. Angiogenesis is one of the important factors in the development of a tumor. Discrete solid tumoral masses appear if the tumor cells can provoke the adjacent vascular network to expand to supply their nutritional needs. Therefore, the factors involved in the stimulation of angiogenesis have been studied for their role in the development of tumor and anti-angiogenic factors as well as drugs having an angiogenic inhibitory activity have been also investigated as tools for controlling the growth or for effecting regression of tumors.

It has been discovered that scapular cartilage in calves contains a substance that inhibits the vascularization of solid tumors (Langer et al., 1976). Because of its encouraging potential as anti-tumor agent, sources of greater supply of cartilage have been looked for.

Sharks are animals being a potential source of this kind of angiogenesis inhibitor because their endoskeleton is composed entirely of cartilage (6% of their body weight versus 0.6% in calves). Sharks have also as an interesting characteristic a low propensity to developing tumors. Many hypotheses have been elaborated to explain this low probability of developing tumors in sharks. Marchalonis et al. (1990) have shown IgM antibodies able to readily attack any aggressing agent. McKinney et al. (1990) have shown that sharks have macrophages capable of differentiating normal cells from neoplastic cells and of destroying the latter. Rosen and Woodhead (1980) have postulated that the rarity of tumors in elasmobranchs (a group to which pertain sharks and rays) might be due to the high ionic strength of their tissues, which is equivalent to a high body temperature. In these conditions, these authors believe that the immune system exerts a close to 100% immunological surveillance. Moore et al. (1993) have discovered that sharks produce an aminosterol having antibacterial and antiprotozoal properties. Finally, Lee and Langer (1983) and Folkman and Klagsbrun (1987) have shown that sharks produce a substance which inhibits neovascularization. Lee and Langer (op.cit.) have isolated this substance by extracting it from shark cartilage in denaturing conditions (guanidine extraction). This process of extraction is however very long (41 days) and might generate extracts having denatured factors. While the active substance isolated from calves has a molecular weight of about 16 kilodaltons (kd), the same group of researchers have not given a precise molecular weight to the one retrieved in sharks. This substance is only defined has having a molecular weight higher than 3500 daltons. Oikawa et al. (1990) have applied the same method of extraction as the one described by Lee and Langer, but of a much shorter duration (2 days instead of 41 days). The substance isolated from shark cartilage by Oikawa et al. has a molecular weight ranging from 1000 to 10000 daltons. Schinitsky (U.S. Pat. No. 4,473,551) has described a water extract of crude powdered shark cartilage which fraction of more than 100,000 Daltons has an anti-inflammatory activity alone or in combination with glucosamine. No suggestion of a component of this extract having an anti-angiogenic or anti-tumor activity is made in this patent. Kuetner et al. (U.S. Pat. No. 4,746,729) have isolated a polymorphonuclear neutrophil (PMN) elastase inhibitor from bovine cartilage. This inhibitor has been obtained from an aqueous extract of cartilage from which molecules of a molecular weight of more than 50,000 Daltons have been retained. Fractionation on Sephacryl S-200 has given numerous fractions from which those of 10–40 kD have been pooled after they have demonstrated an anti-elastase activity. The active component has an isoelectric point of 9.5 and might have a molecular weight of about 15,000 Daltons. Kuetner et al. (U.S. Pat. No. 4,042,457) have also shown that bovine cartilage has a component of a molecular weight of less than 50,000 Daltons which has a cell proliferation inhibitory activity without any activity on endothelial cell growth. Spilburg et al. (U.S. Pat. No. 4,243,582) have isolated two glycoproteins of molecular weight of 65 KD and of pI 3.8 from bovine cartilage (guanidine-extraction) which show anti-trypsin activity and an endothelial cell growth inhibitory activity.

Calf and shark cartilage contain many biological activities such as lysozyme activity, cell growth-promoting activity, inhibitory activity against types I and IV collagenase, elastase, and against proteases like trypsin, chymotrypsin and plasmin.

Methods of obtaining a shark cartilage extracts and fractions are already known. Some of them produce a powdered crude cartilage without any extraction (U.S. Pat. No. 5,075,112), others use denaturing agents like guanidine (U.S. Pat. No. 4,243,582), or enzymatic reaction to get rid of any muscular, nervous or vascular structures surrounding the cartilage and organic solvents to eliminate fats (U.S. Pat. Nos. 3,478,146, 4,350,682 and 4,656,137) and to obtain an extract of cartilage, while others simply produce aqueous extracts (in water (U.S. Pat. No. 4,473,551) or salt solutions (U.S. Pat. No. 4,746,729)) of cartilage by eliminating the unsolubilized material. Among the latter, specific fractions of specific molecular weights have been particularly retained for further study and purification (see discussion above).

Summing up, shark cartilage is known as containing anti-angiogenic component(s) generally tested in rabbit corneal pocket assay or in chick chorioallantoic membrane (CAM) assay. Up to date, whole powdered cartilage has been tested directly on tumors in vivo, on human melanoma xenograft implanted in nude mice (U.S. Pat. No. 5,075,112), as well as tested in CAM for its anti-angiogenic effect. However, no evidence has been brought to a direct effect of cartilage extract on tumor cells.

Angiogenesis is not only involved in cancer development. Many diseases or conditions affecting different physiological systems (indicated in parentheses) are angiogenesis-dependent among which the following examples: arthritis and atherosclerotic plaques (bone and ligaments), diabetic retinopathy, neovascular glaucoma, trachoma and corneal graft neovascularization (eye), psoriasis, scleroderma, hemangioma and hypertrophic scarring (skin), vascular adhesions and angiofibroma (blood system). Therefore, any new anti-angiogenic factor could find a use in the treatment of these diseases as well as in cancer therapy.

STATEMENT OF THE INVENTION

The present invention relates to a method of producing extracts having anti-angiogenic properties (reduction of the area of blood vessels observed in vivo on experimentally induced tumors), tumor regressive activity in vivo as well as demonstrating a direct inhibitory effect on tumor cell lines. These extracts come from the cartilage of sharks commonly called Common Spiny dog Fish and Black Spiny dog fish (*Squalus acanthias*). This process does not involve any denaturing solvent or product and does not involve the use of any enzymes. It consists of obtaining a blend of whole cartilage in an aqueous solution of neutral pH, preferably pure water, this blend being centrifuged and the pellet and supernatant kept for further processing. The pellet is lyophilized and tested for anti-tumor and anti-angiogenic activities in vivo and in vitro, with or without supernatant. The supernatant has been shown to have anti-angiogenic and tumor regressive activities in vivo. The composition of the supernatant has then been investigated by different ways. Fractionation of this supernatant led to the characterization of some of its active components. The fractions were tested for their direct in vitro activity on cancer cell lines. Therefore, it is assumed that the non-fractionated supernatant has such an in vitro activity. Lyophilization substantially destroys the activity of these fractions and it should be emphasized that a clear difference is made between solid and liquid extracts and fractions thereof.

This invention also relates to a cartilage lyophilizate or solid extract, a liquid cartilage extract and to liquid fractions thereof, as well as a process for the obtention of all of them.

Finally, this invention relates to the use of cartilage extracts in the treatment of angiogenesis-dependent diseases. Preliminary clinical trials have shown the efficacy of pharmaceutical compositions containing a concentrated unfractionated liquid extract in the improvement of the condition of patients suffering of angiogenesis-dependent diseases. Among them, dermatological disorders like psoriasis and one case of prostate cancer were successfully tested. Acne which is another dermatological disorder not documented as an angiogenesis-dependent disease has been also surprisingly successfully treated. The excessive neovascularization is a recognized feature of hypertrophic scarring in burned patients. Compositions containing the cartilage extract of the present invention are currently tested to prevent this phenomenon. Pharmaceutical compositions containing as an active ingredient the liquid cartilage extract are also an object of this invention.

BRIEF DESCRIPTION OF THE FIGURES

The present invention will be more readily understood by the following specific embodiments which are complemented by the following figures, which purpose is to illustrate the invention rather than to limit its scope:

FIGS. 3a) and b) show a comparison of liver sections of rats having developed a mammary gland cancer which have been administered by gavage a combination of cartilage lyophilizate and supernatant and those which have been administered only water. Cytoplasm and nuclei of parenchymal cells show a normal appearance (Magnification=200×).

FIGS. 4a) and b) show a comparison of kidney sections of rats having developed a mammary gland cancer which have been administered by gavage a combination of cartilage lyophilizate and supernatant and those which have been administered only water. All the tubular cells appear normal with clear and well delimited cytoplasm. The tubular lumen are empty and no desquamated cells are present therein (Magnification=200×).

FIGS. 5a) and b) show a comparison of lung sections of rats having developed a mammary gland cancer which have been administered by gavage a combination of cartilage lyophilizate and supernatant and those which have been administered only water. The wall of a bronchiole (B) and of alveoli (A) appear intact with well delimited epithelial cells. Lumen are free of desquamated cells (Magnification=200×).

FIGS. 6a) and b) show a comparison of mammary gland tumor sections of rats having developed such a tumor which have been administered by gavage a combination of cartilage lyophilizate and supernatant and those which have been administered only water. In FIG. 6a), blood vessels are numerous and some of them (v) are large. In FIG. 6b), a decrease in the number and size of blood vessels (v) is observed. This provides the appearance of a more compact tissue (Magnification=120×).

FIGS. 9a) and 9b) illustrate the significant improvement of the condition of a patient suffering of psoriasis complicated with hyperkeratosis, when treated with a topical composition containing an effective amount of concentrated liquid cartilage extract (FIG. 9b) compared with his initial condition (FIG. 9a)).

FIGS. 10a) and 10b) illustrate a remarkable improvement of the condition of a patient suffering of psoriasis non-complicated with hyperkeratosis, when treated with a topical composition containing an effective amount of concentrated liquid cartilage extract (FIG. 10b)) compared with his initial condition (FIG. 10a)).

DESCRIPTION OF THE INVENTION

Figure 1:
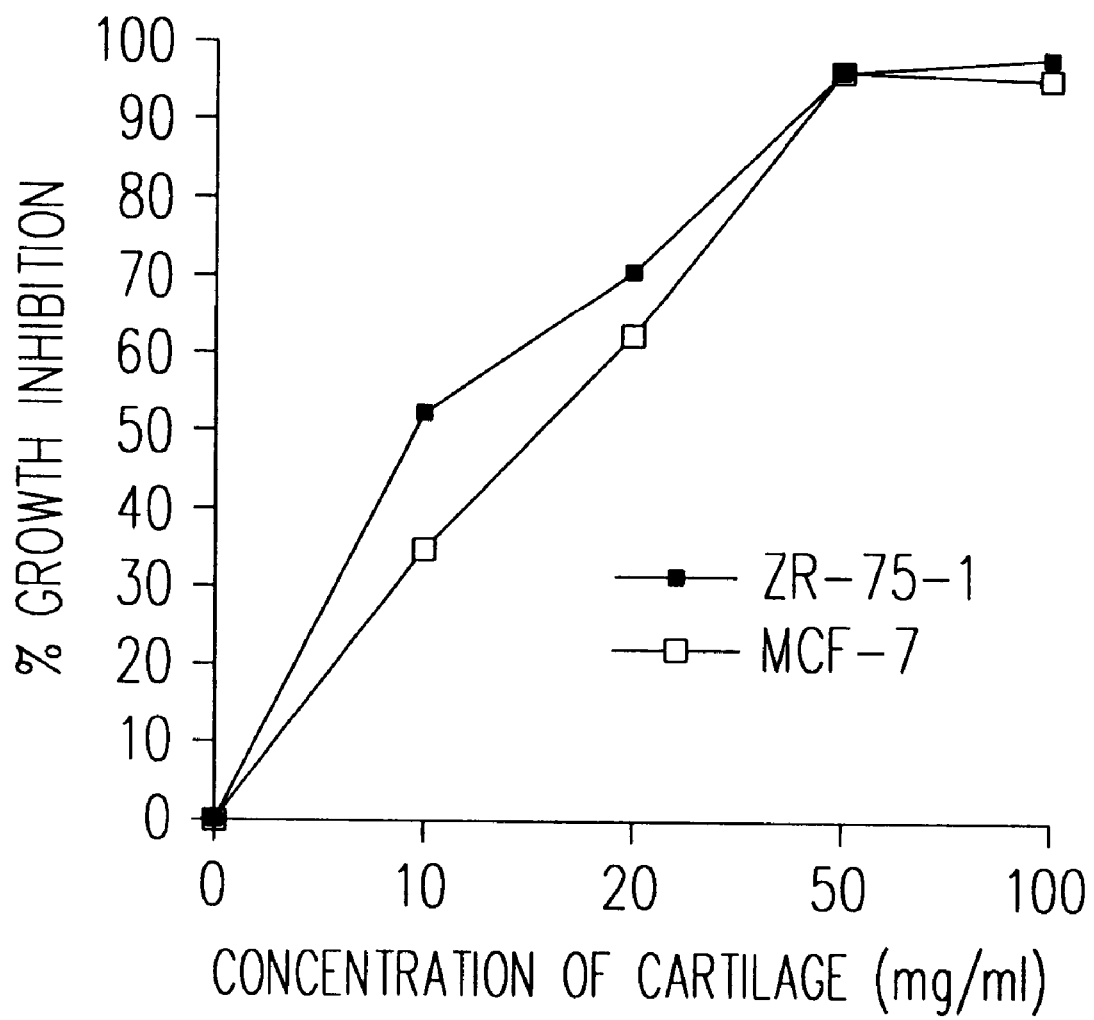
FIG. 1 shows the inhibitory activity of increasing doses of shark cartilage (solid extract) on ZR75-1 and MCF-7 cells.

After their capture, cartilage has been obtained from healthy sharks Black Spiny Dog Fish and Common Spiny Dog Fish. Any muscular and connective tissue has been removed by scraping with ethanol-treated scalpels and scissors. The cartilage was then vacuum-packed in plastic bags and frozen to −20° C. for further use.

Preparation of Lyophilized Cartilage

Cartilage was thawed to 4° C. Cartilage was then passed three times through the pores of an ethanol-treated meat chopper together with an equal quantity (weight/volume) of water which has been purified by inverse osmosis and filtration on a 0.1 $\mu$m filter, to obtain a first blend. Many aqueous solutions could be used in lieu of water as far as a neutral pH is preserved to avoid lysis or denaturation of the cartilage components.

This blend was then made homogenized by an agitation at a maximal speed in an industrial blender at 4° C. during ten minutes. A liquefaction of this homogenate was obtained by submitting the latter to Polytron disintegrator during 10 minutes at 4° C. At this step, residual particle size is less than 500 $\mu$m. This blend was centrifuged at 13,600×g during 15 minutes at 4° C. The resulting pellet was lyophilized for 24 to 48 hours. This first fraction will hereinbelow be defined as the lyophilizate or a solid extract.

The supernatant was filtered on a 24 µm Whatman filter to get rid of particles susceptible to affect the performance of an ultrafiltration column. The filtrated material was then ultrafiltrated at 4° C. on an tangential flow filtration column having a porosity of 500 000 Daltons. This supernatant was sterile filtered on 0.22 µm filter, aliquoted in sterile bottles for further use. This fraction will be further referred to as the supernatant or the liquid extract.

An alternative, higher performance procedure has been developed to obtain the lyophilizate and the supernatant. The step of centrifuging at 13600×g for 15 minutes followed by a gross filtration on Whatman filters has been replaced by a centrifugation in a CEPA centrifuge equipped with a nylon pocket of a porosity of 30 µM, at 3000–4000×g. A 20 kg/20 L preparation can be centrifuged in that manner within 30 minutes and provide 21 liters of supernatant. The aqueous volume obtained is even higher than the starting volume of water, which means that even a part of the water content of the cartilage itself has been harvested. The lyophilizate and the supernatant may have the following composition:

| LYOPHILIZATE: | |
| --- | --- |
| Lipids | 7.35%[1] |
| Proteins | 46.2%[2] |
| Humidity | 20.4% |
| Sodium | 4.16 mg/g[3] |
| Potassium | 2.64 mg/g |
| Calcium | 114 mg/g |
| Magnesium | 1.49 mg/g |
| Zinc and iron traces | |
| SUPERNATANT: | |
| Lipids | 0.10%[1] |
| Proteins | 8 mg/ml[2] |
| Humidity | 98.8% |
| Sodium | 33.6 mg/100 g[3] |
| Potassium | 39.2 mg/100 g |
| Calcium | 2.0 mg/100g |
| Magnesium | 1.1 mg/100 g |
| Zinc and iron traces | |

[1,2]Measured following directives published in AOAC Official (1984) sections 16.219–220 and 2.055, respectively;
[3]Measured following the SAA procedure.

The protein content is evaluated by the Kjeldahl method, which indeed measures organic nitrogen (N). Organic nitrogen is converted to equivalent protein by using the following equation:

$$\text{Proteic content (mg/mL)} = \frac{\% N \times 6.25}{100}$$

Carbohydrates being not detectable, one can presume that they are in one or another extract but under the form of proteoglycanes and/or mucopolysaccharides. It is possible that these compounds are included in the measured level of humidity. The lyophilizate contains an unexpected level of humidity which was measured by the OH– groups. Since the 20% water content is close to the percentage of carbohydrates normally retrieved in cartilage while the humidity of a lyophilizate should be close to 0%, this hypothesis remains to be verified.

Sterility has been controlled, applying USP XX11 specifications by:
  1) Laboratoire de genie sanitaire du Québec Inc. 1090, l'Escarbot, Centre Industriel St-Malo, Québec G1N 4J4; and
  2) Northview Laboratories Inc. 1880, Holste Road, Northbrook, Ill., 60062 U.S.A. FDA registration no. 14-18028

Activity assays:
LYOPHILIZATE:
  In vitro assays:
    These assays have been conducted on the hormono-dependant cancer cell lines MCF-7 and ZR75-1 (ATCC (R) numbers 22-HTB and 1500-CRL, respectively).
  ZR75-1 cells:
    BASAL RPMI medium:
      52 g RPMI 1640 without phenol red (Sigma R8755), 17.875 g Hepes (free acid; Sigma H0763), 0.55 g sodium pyruvate (Sigma P5280) and 10 g NaHCO$_3$ were mixed in 5 L of pure water and made pH 7.40 with NaOH.
      If not used immediately, this solution must be protected from light to preserve photolabile substances. This solution was filtered, distributed in 500 mL sterile bottles and stored at 4° C. for a maximal period of three months.
    Cell culture maintenance medium:
      Basal RPMI medium was supplemented with 10% (v/v) FBS (fetal bovine serum), 100 U penicillin G/50 µg streptomycin sulfate (Sigma P0906)/ml medium, 2 mM L-Glutamine (Sigma G1517) and 1 nM $E_2$ (β-estradiol Sigma E8875).
    Experimental medium:
      Basal RPMI medium was supplemented with 5% FBSA (fetal bovine serum adsorbed on dextran-charcoal), 2 mM L-Glutamine, 100 U penicillin G/50 µg streptomycin sulfate/ml medium and 50 ng/mL insulin (Sigma). To this medium was added increasing concentrations of the above-described lyophilizate as well as different concentrations of estradiol ($10^{-12}$ to $^{-5}$ M).
  MCF-7 cells:
    BASAL DME-F12 medium:
      DME-F12 medium (without bicarbonate and without red phenol; Sigma) was reconstituted following the manufacturer's directives in pure water. For one liter, 1.2 g of sodium bicarbonate was added and the pH made to 7.40 with NaOH/HCl. This solution was filtered, distributed in 500 mL sterile bottles and stored at 4° C. for a maximal period of three months.
    Cell culture maintenance medium:
      Basal DME-F12 medium was supplemented with 10% (v/v) FBS (fetal bovine serum), 100 U penicillin G/50 µg streptomycin sulfate/ml medium, 2 mM L-Glutamine (Sigma) and 1 nM $E_2$ (estradiol).
    Experimental medium:
      Basal DME-F12 medium was supplemented with 5% FBSA (fetal bovine serum adsorbed on dextran-charcoal), 2 mM L-Glutamine, 100 U penicillin G/50 µg streptomycin sulfate/ml medium and 50 ng/mL insulin (Sigma). As described for the ZR75-1 cells, lyophilizate and estradiol were added at the same concentrations.
Preparation of FBSA:
  Fetal bovine serum was mixed with 1% (w/v) charcoal (carbon decolorizing alkaline). A solution of dextran T70 was added to the charcoal-serum solution to achieve a concentration of 0.1% (w/v). The mixture was agitated overnight at 4° C. After centrifugation at 4° C. for 30 minutes at 10,000×g, the serum was decanted, mixed again with the same proportions of charcoal and dextran, agitated at room temperature for three hours and re-centrifuged. The serum was then heat-inactivated at 56° C. for 20 minutes, sterile filtered and aliquoted in sterile conical Falcon tubes.
  ZR75-1 and MCF-7 cells were grown to reach a density of population of 20 000 cells/well on 24-well plaques or 150

000 cells/well on 6-well plaques, and treated in the presence or absence of different concentrations of lyophilizate as prepared above. All experiments have been performed in triplicates. Culture media have been withdrawn and replaced by fresh media every two days. Cells were grown in an incubator under a constantly humidified atmosphere containing 5% $CO_2$, at 37° C., for 17, 7, 3 or 3 days, corresponding to the first, second, third or fourth experiment, respectively. Cell growth inhibition was measured by direct counting of the cells or by measuring the total DNA content of a well.

| Concentration of lyophilizate | Cell Inhibition (%) | |
| --- | --- | --- |
|  | MCF-7 | ZR75-1 |
| 1st experiment: 17 days | | |
| 1 mg/ml | 1.5 | 2.00 |
| 5 mg/ml | 14.33 | 33.6 |
| 10 mg/ml | 62.66 | 90.8 |
| 2nd experiment: 7 days | | |
| 1 mg/ml | 3.73 | 0.97 |
| 5 mg/ml | 15.7 | 29.00 |
| 10 mg/ml | 68.37 | 66.00 |
| 3rd experiment: 3 days | | |
| 50 mg/ml | 95.8 | 95.00 |
| 100 mg/ml | 94.6 | 98.00 |
| 4th experiment: 3 days | | |
| 10 mg/ml | 34.4 | 51.5 |
| 20 mg/ml | 62.5 | 70.5 |
| 50 mg/ml | 95.8 | 95 |
| 100 mg/ml | 94.6 | 98 |

The above percentages of inhibition of cell growth demonstrate that the lyophilizate can inhibit in a dose-dependent manner the growth of the cells of these two cell lines.

FIG. 1 shows that doses of 50 and 100 mg/mL of the lyophilizate clearly provoke hypoplasia on these cell lines, after three days of treatment.

Figure 2:
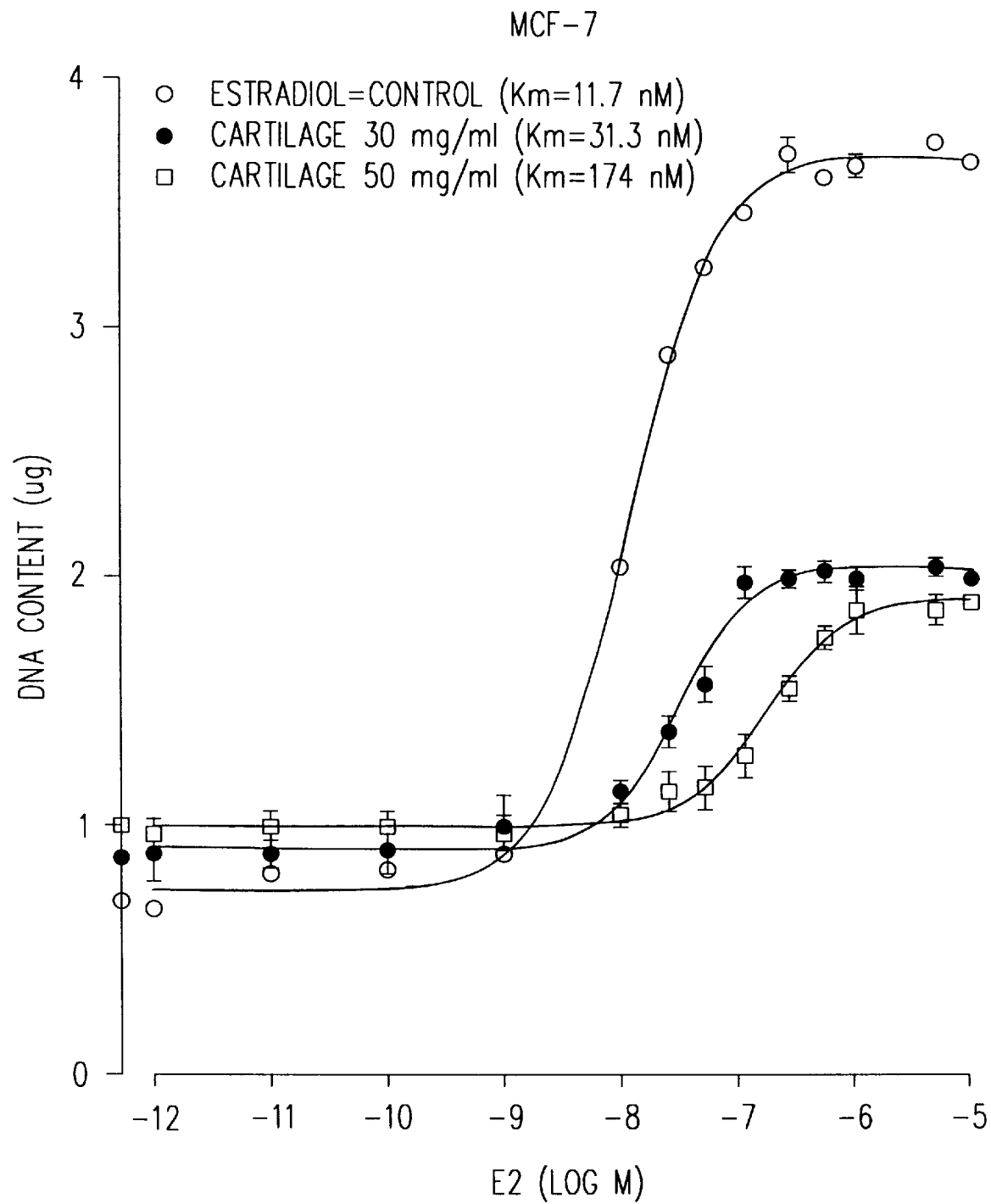
FIG. 2 illustrates dose-response curves of the quantity of MCF-7 cells measured by their DNA content in the presence of increasing concentrations of estradiol with or without two concentrations of cartilage lyophilizate.

FIG. 2 shows that, in the presence of $10^{-12}$ to $10^{-9}$ M estradiol, treated cells respond like control cells by being non-stimulated by these hormone dosage rates. However, above 1 nM, control cells are strongly stimulated, and concentration of DNA reach 3.75 ug in the presence of $10^{-7}$ M estradiol (versus 0.69 ug in control without estradiol). In cells treated with 30 and 50 mg/mL of lyophilizate, DNA measured at the maximal stimulation is 1.9 and 1.8 µg, respectively. FIG. 2 shows that the affinity constant (Km) of the treated cells for estradiol is 3 and 16 times higher than the value of Km of the control cells, in the presence of 30 and 50 mg/mL, respectively. This means that higher concentrations of estradiol are necessary to achieve the same growth of the cells when cartilage lyophilized solid extract is present. Therefore, this extract diminishes the maximal response (90% inhibition thereof) and increases the affinity constant of the treated cells to estradiol.

In vivo assays:

Four hundred 40 day old female Sprague-Dawley rats (purchased from Charles River Co., St-Constant, Québec) where adapted to their environment for 12 days. At that time, 20 mg DMBA/1 mL corn oil (9, 10-Dimethyl-1, 2-Benzanthracene; purchased from Sigma Chemical Co.) was administered by gavage. Three months after this treatment, 240 rats having developed a mammary breast cancer have been selected and distributed in two groups. The first group consisted of five sub-groups of rats. The rats of the treated groups were given a daily dose of increasing concentrations of the lyophilizate extract in 3 mL of water for eight weeks while the control group received the same volume of water. The second group consisted in four sub-groups of rats. The rats of the treated groups were also given a daily dose of the lyophilizate in 3 mL of water (about 25 mg of protein) combined with or without the supernatant, for ten weeks while the control group received the same volume of water. Only one sub-group of the second group of rats treated with a concentration of 3000 mg/Kg/day of the lyophilizate and 3 mL of the supernatant was also given an intraperitoneal (i.p.) injection of a smaller dose of the supernatant (about 8 mg of protein in 1 mL of water).

Rats were weighing 151–175 g at the beginning of the two experiments and received feed and drinking water ad libitum. The first group of rats had a tumor of average diameter of 0.9 cm while the second group of rats had a tumor of average diameter of 0.6 cm.

The results are summarized as follows:

| Daily doses of cartilage extract administered by gavage | % tumor growth inhibition (decrease of tumor diameter vs control) |
| --- | --- |
| 1st experiment: duration 8 weeks | |
| 500 mg/Kg/day | 2% |
| 1000 mg/Kg/day | 4% |
| 3000 mg/Kg/day | 14% |
| 5000 mg/Kg/day | 15% |
| 2nd experiment: duration 10 weeks | |
| 3000 mg/Kg/day | 12% |
| 3000 mg/Kg/day + 3 ml supernatant | 18% |
| 3000 mg/Kg/day + 3 ml supernatant + 1 ml inj. i.p. supernatant | 20% |

These results demonstrate that the lyophilizate contains an active component which is absorbed in the gastro-intestinal tract and which has an effect on tumor size. This effect might be a direct effect on tumor cells or an anti-angiogenesis mediated effect.

These results also show that the supernatant has an activity which is reflected by a supplementary reduction of tumor size of about 5%, even though it is very diluted (the quantity of proteins present in 3 ml of supernatant is about 25 mg).

Histopathology

For evaluating the non-toxicity of the active molecules of the cartilage extract, the animals used in the above in vivo experiments were killed by decapitation and the following tissues were taken for analysis: liver, lung, kidneys, heart, brain, muscle and mammary gland. Fat was taken out of these tissues, after what they were fixated for two days in Bouin fluid. After dehydration in ethanol, the fixated tissues were embedded in paraffin. Sections thereof were obtained and mounted on glass slides, colored with haematoxylin and visualized under microscope.

The histological examination revealed that no deleterious effect was visible when using the largest doses of lyophilizate alone (data not shown) or when using the lyophilizate in combination with the supernatant (see FIGS. 3a and b, 4a and b, and 5a and b).

This suggests that the lyophilizate and the supernatant have a selective tumor size regressive activity.

Figure 7:
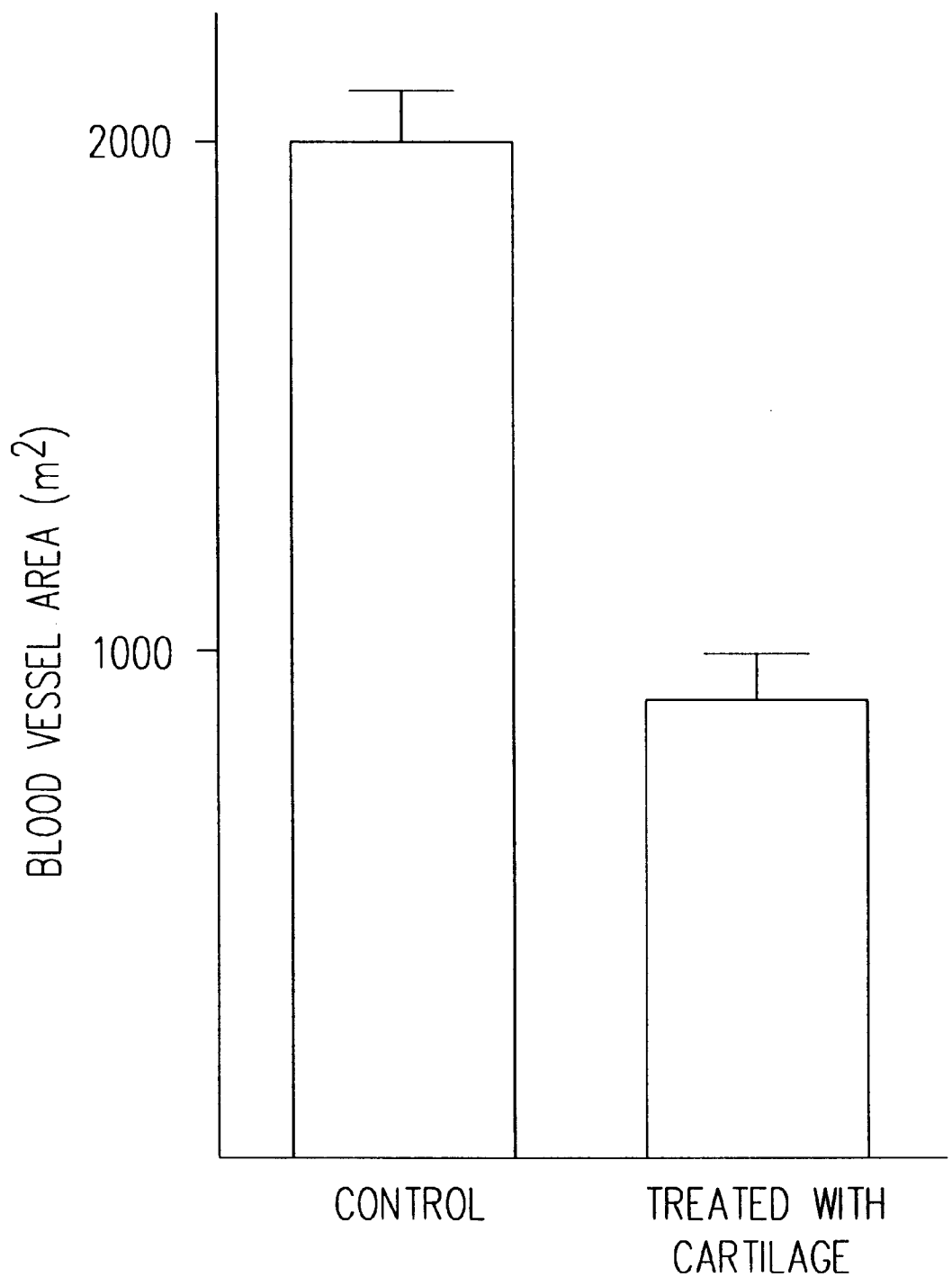
FIG. 7 is an histogram derived from FIGS. 6a) and b), illustrating the effect of cartilage extract on blood vessel area in tumors.

In cancerous mammary gland (see FIGS. 6a and b), an important diminution of the area of blood vessels was observed. The anti-angiogenic effect of these active molecules is then confirmed by results as illustrated and summarized in the following picture and histogram:

FIG. 7 shows that, when a combination of lyophilizate (p.o.)-supernatant (p.o.+i.p.) was used (refer to FIGS. 6a and b), a decrease of 55% of the blood vessel area was observed.

The diminution of the tumor size might be due to an important decrease in its vascularization, to a direct effect of tumor cells, or a combination of both phenomenons. The anti-angiogenic effect of these extracts is well depicted above. The direct hypoplasiant effect has been observed in vitro on the hormono-dependent cells, which remains to be confirmed in vivo.

Because the above-mentioned results showed that the supernatant had an increased effect over and above the effect of the lyophilizate on ZR75-1 cells, the components thereof were further investigated.

Obtention of Liquid Fractions Containing Active Molecules

Shark cartilage was harvested and processed the same as described above except for the concentration step which has been omitted. After centrifugation, the pellet was discarded and the supernatant was processed the same way as described above up to the sterile filtration on 0.22 µm filter.

The supernatant will be hereinbelow referred to a crude permeate, e.g. the product after the ultrafiltration.

The so obtained crude permeate was passed on FPLC (Fast Protein Liquid Chromatography).

FPLC conditions:

Column: Hiload 26 mm×60 cm SEPHACRYL S-300

FPLC system: from Pharmacia

All samples were filtered on 0.22 µm filter before loading on the column. The elution buffer was phosphate buffer saline (PBS) filtered and degazed during 15 minutes. The volume of the loaded sample was usually 3.2 mL (could be up to 13 mL). The flow rate was 1 mL/minute. Fractions of 10 mL were collected. The eluted compounds were detected by their U.V. absorbance (280 nm). A calibration chart was obtained by using the MW-GF-1000 calibration kit from Sigma, this calibration sample having the same volume as the loaded sample to analyse (3.2 mL). The elution volume of a sample was deduced from the plotting of the molecular weight of the compounds of the calibration kit versus their elution volume to which was subtracted the void volume of the column. The void volume was obtained by injecting dextran blue (M.W.=2,000,000). The fractions were tested on ZR75-1 cells for their activity. The fractions of interest were identified and their characteristics were corroborated by further study (hereinbelow).

Additional characterization of the active components of the permeate was conducted on Rotofor (Biorad 170-2950; see isoelectrofocalization below) and on Amicon filters of different cut-off values to obtain fractions of molecular weight of between 10–30 KD, 30–100 KD and more than 100 KD.

Isoelectrofocalization:

A preparation of shark cartilage (46 mL of permeate 1 Kg/L) was dialysed overnight against 4 liters of pure water containing 5% glycerin at 4° C. using a membrane Spectra pore #7 MWCO 3500 KD (Spectrum 132110). The dialyzed solution was mixed with 2.75 mL of ampholytes (Pharmacia #80-1125-87) pH 3.5–10.0 and 0.5 g chaps (Sigma C3023; 3- [(3-Cholamidopropyl) -dimethylammonio]-1-propane-sulfonate). The volume was completed to 55 mL with pure water. The solution was loaded on Rotofor. Isoelectrofocalization was conducted at 4° C., at a constant power of 12 watts (3000 xi power supply Biorad 165-0554), under constant water circulation for insuring maintenance of the temperature. At the beginning of the separation, the voltage was 380 volts and the amperage 31 mA. When the amperage was stabilized (at 14 mA), the voltage read 870 volts. The isoelectrofocalization was stopped and 20 fractions were collected.

| FRACTION | VOLUME (mL) | pH |
|----------|-------------|-------|
| 1 | 3.7 | 3.56 |
| 2 | 2.1 | 4.01 |
| 3 | 2.2 | 4.18 |
| 4 | 2.3 | 4.31 |
| 5 | 2.2 | 4.63 |
| 6 | 2.1 | 5.03 |
| 7 | 2.5 | 5.30 |
| 8 | 2.1 | 5.50 |
| 9 | 2.4 | 5.81 |
| 10 | 2.5 | 6.26 |
| 11 | 2.3 | 7.00 |
| 12 | 2.4 | 7.29 |
| 13 | 2.4 | 7.64 |
| 14 | 2.5 | 7.94 |
| 15 | 2.3 | 8.32 |
| 16 | 2.5 | 8.62 |
| 17 | 2.4 | 8.94 |
| 18 | 2.9 | 9.30 |
| 19 | 3.1 | 9.88 |
| 20 | 3.6 | 10.71 |

The identification of these proteins was made by estimating their molecular weight on an electrophoresis gel (Laemmli, U.K. (1970) Nature (Lond.) 227: 680).

Figure 8:
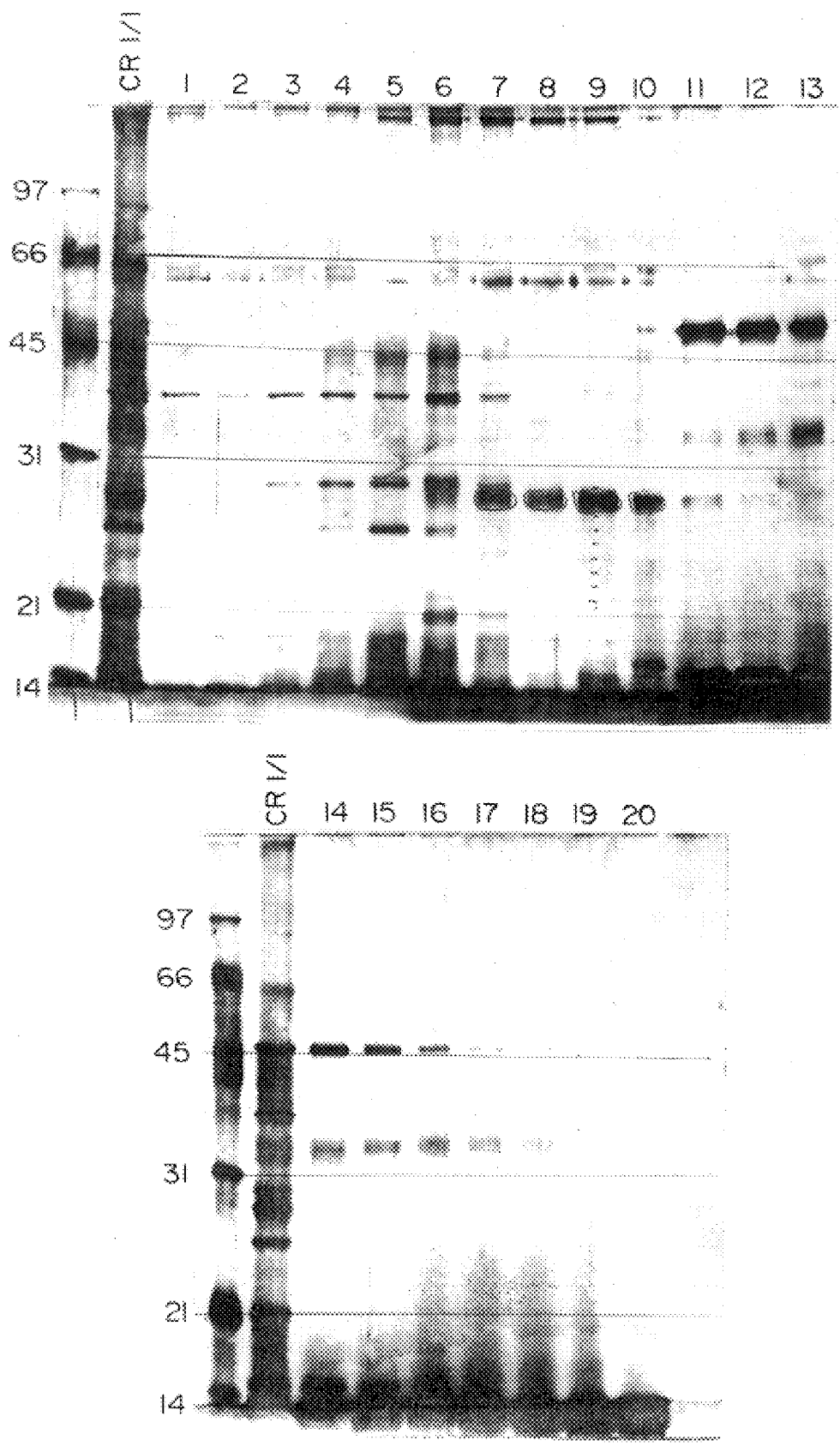
FIG. 8 represents the electrophoretic profile in non-denaturing conditions of liquid fractions separated on Rotofor; molecular weight markers appear at the left followed by a sample of the crude permeate before fractionation, for comparison with the isolated fractions.

These fractions were four-fold diluted with a loading buffer (see Laemmli) and 8 µL aliquots were submitted to electrophoresis in non-reducing conditions. FIG. 8 shows the electrophoretic profile of each fraction and of the material before isoelectro-focalization.

All the fractions were sterile-bottled under a laminar flow hood by passing them through a sterile Millipack-60 filter having a porosity of 0.22 µm.

The protein content of the fractions was evaluated by the Lowry dosage method. Solutions of 1 Kg/2 L (expressed as the crude cartilage weight per liter of permeate were tested on ZR75-1 cells at different concentrations in culture medium. The results are summarized as follows:

$1^{st}$ test:

The permeate was lyophilized and passed on FPLC. No hypoplasiant activity was detectable (data not shown).

$2^{nd}$ test:

Tests performed on Rotofor fractions: Protein identification

| Fractions Identified | Isoelectric Point | Median Value | Molecular Weight |
|----------------------|-------------------|--------------|------------------|
| 7-8-9-10 | 5.30 to 6.26 | 5.78 | 29 + 1 KD |
| 7-8-9 | 5.30 to 6.26 | 5.68 | 60 + 1 KD |
| 12-13-14 | 7.29 to 7.94 | 7.62 | 48 + 1 KD |
| 13-14 | 7.64 to 7.94 | 7.79 | 35 + 1 KD |

3$^{rd}$ Test performed on FPLC fractions:

| Fractions | Molecular weight |
|---|---|
| 6 and 7 | 1–2.5 KD |

4$^{th}$ test performed on 100 μL fractions obtained on Amicon molecular filters:

| Concentration tested | Molecular Weight | Inhibition of ZR75-1 Cell Cultures |
|---|---|---|
| 100 μg/mL | MW > 100 KD | 64% |
| 100 μg/mL | 30 KD < MW < 100 KD | 114% |
| 100 μg/mL | 10 KD < MW < 30 KD | 127% |
| 400 μg/mL | MW < 10 KD | 149% |

FPLC fractions 6 and 7 contain active components of a very small molecular weight: 1 to 2.5 KD.

The hypoplasiant effect of the fractions can be up to 33 000 times higher than the one observed with the lyophilizate. The above results show that lyophilization substantially destroys and/or inhibits the activity of the proteins contained in the eluate while no such abolition occurred when lyophilizing the solid extract.

Further identification of the active components of the eluate:

The active fractions (tested on ZR75-1 cells) are retrieved in the following range of molecular weights, determined by another type of purification starting with the same permeate (1 Kg/L) on a 10 mm diameter×30 cm length Superose-12 column using the FPLC and rotofor procedures described above. A flow rate of 1 mL/minute was selected. 45 fractions of 1 mL were collected.

| Fractions 20–21 | activity in fractions corresponding to a molecular weight of 70 to 120 KD |
|---|---|
| Fraction 22 | activity in fractions corresponding to a molecular weight of 60 to 70 KD |
| Fractions 29–32 | activity in overlapping fractions corresponding to a molecular weight of 35 to 46 KD |
| Fractions 34–35 | activity in fractions corresponding to a molecular weight of 29 KD |
| Fractions 38–39 | activity corresponding to a molecular weight of 1 to 2.5 KD |

Specificity

In order to evaluate the specificity of activity on tumor cells, the permeate obtained after ultrafiltration was tested on other mesenchyme originating cells, human TENON fibroblasts (HTFs), which are normal fibroblasts.

B. In Vitro a. Patients

Only the HTFs from two patients (one with neovascular glaucoma, NVG, and the other with primary open angle glaucoma, POAG) have been used.

b. Subculturing and Maintenance of HTFs

Each confluent culture were passaged by washing and detaching with 0.5 ml of 0.05% trypsin/0.5 mM EDTA (Gibco 610-5300 AG) for 5–10 minutes at 37° C. 1.5 mL of DME/F-12 medium containing 15% FBS was then added to neutralize trypsin/EDTA.

Association of the cells was made by triturating and transferring into 25 cm$^2$ T-flasks, into which additional medium containing 10% FBS was added. After confluence was reached, the HTFs were transferred into 75 cm$^2$ and eventually, into 180 cm$^2$ T-flasks. When enough cells were obtained, some cells were utilized for the experiments as described below, and others were simultaneously frozen to preserve identical passages for future experiments.

c. Experimental Protocols

When confluence was reached, cells from one patient growing in two or three identical 180 cm$^2$ T-flasks were dissociated by the procedure described above. After a short low speed centrifugation, they were counted with a ZMI Coulter Counter 216013, equipped with a 256-Channelyzer.

For all of the in vitro experiments which follow, approximately fifty thousand cells were inoculated in 1 mL of DME/F-12 medium containing 1% FBS into each 16 mm dish and a 12-well plate. Seventeen hours (hrs) after seeding, 1 mL of fresh identical medium supplemented with 1% FBS ("absolute" controls) was added. Depending on the experimental design (see above and below), the 1% FBS medium was supplemented or not with a GFs (Growth Factors) or with the permeate 1 Kg/2 L (cartilage weight/water volume) solution and sterile filtered. On this day (day 0), some samples of cells were also counted to determine plating efficiency (which should be equal or greater than 95%).

Forty-eight hours after the onset of the experiments, the cells were rinsed and dissociated by the afore-mentioned procedure and counted again. The number of cells was expressed as a percentage of that obtained in the "absolute" controls.

Each "absolute" or positive control, containing 1% or 5% FBS, respectively, and each experimental group, supplemented with 1% FBS and with an individual GF or cartilage permeate consisted of triplicate samples.

Each experiment was carried out on the cells of one or two patients at a time, and was repeated at least twice.

Stimulation of fibroblast proliferation by growth factors (GFs) or cartilage permeate was compared to the stimulation of the same by 5% FBS.

In these experiments, GFs, porcine PDGF (pPDGF) and human recombinant bFGF, hr bFGF (gift to Dr. P. Brazeau from Farmitalia Carlo Erba, Milan, Italy) were added in concentrations of 10 to 100 ng/ml in 1% FBS, respectively. Forty-eight hours after the onset of the experiment, the cells were dispersed by Trypsin-EDTA and counted on the Coulter counter. All triplicate values (columns 1, 2 and 3) appearing below equal one twentieth of counts per well.

Patient B: Glaucoma Sexe: Male Age: 53
HTF
Day −1: number of cells per well: 46170
DME/F12 - 1% FBS - 1% Pen. Strep
Day 0: number of cells per well: 65214
DME/F12 - 1% FBS - 1% Pen. Strep
Day 1: number of cells per well: 62548
DME/F12 - 1% FBS - 1% Pen. Strep
Day 2: number of cells per well:
DME/F12 - 1% FBS - 1% Pen. Strep

|  |  | Sample/plate | 1 | 2 | 3 | AVE. | SEM | % control growth |
|---|---|---|---|---|---|---|---|---|
| Plate #1 FBS |  | DME/F12 |  |  |  |  |  |  |
|  | 1 | Day 0 1% FBS | 3,019 | 2,862 | 2,853 | 65,214 | 71 |  |
|  | 2 | Day + 1 1% FBS | 2,711 | 2,973 | 2,693 | 62,548 | 1,655 |  |
|  | 3 | Day + 2 1% FBS | 2,284 | 2,400 | 2,191 | 51,333 | 1,655 | 100 |
|  | 4 | Day + 2 5% FBS | 3,084 | 2,834 | 3,115 | 67,446 | 1,627 | 131 ‡‡ |
| Plate #2 PDGF |  | DME/F12 |  |  |  |  |  |  |
|  | 5 | Control (1% FBS) | 2,558 | 2,181 | 2,216 | 51,931 | 2,199 | 100 |
|  | 6 | 1 ng/ml 1% FBS | 2,425 | 2,580 |  | 56,056 | 1,228 | 108 |
|  | 7 | 10 ng/ml 1% FBS | 4,080 | 3,975 | 4,282 | 92,116 | 1,648 | 177 ‡‡‡ |
|  | 8 | 100 ng/ml 1% FBS | 4,625 | 4,356 | 4,450 | 100,285 | 1,442 | 193 ‡‡‡ |
| Plate #3 b-FGF |  | DME/F12 |  |  |  |  |  |  |
|  | 9 | Control (1% FBS) | 2,915 | 2,533 | 2,502 | 59,360 | 2,429 | 100 |
|  | 10 | 1 ng/nl 1% FBS | 2,744 | 2,554 | 2,761 | 60,174 | 1,213 | 101 |
|  | 11 | 10 ng/ml 1% FBS | 3,606 | 3,143 | 3,193 | 74,234 | 2,683 | 125 |
|  | 12 | 100 ng/ml 1% FBS | 4,064 | 3,033 | 3,026 | 75,585 | 6,307 | 127 |
| Plate #4 CARTILAGE (1 Kg/2L) (filtered) |  | DME/F12 |  |  |  |  |  |  |
|  | 13 | Control (1% FBS) | 2,826 | 2,566 | 2,486 | 58,822 | 1,877 | 100 |
|  | 14 | 1 μl/ml 1% FBS | 2,729 | 2,576 | 2,575 | 58,837 | 936 | 100 |
|  | 15 | 10 μl/ml 1% FBS | 2,643 | 2,493 | 2,584 | 57,643 | 798 | 98 |
|  | 16 | 100 μl/ml 1% FBS | 2,918 | 2,883 | 2,766 | 58,483 | 2,461 | 99 |

‡‡ P < 0.02
‡‡‡ P < 0.01 Determined by Student-Fisher Test

While growth factors like PDGF (Platelet-Derived Growth Factor) and bFGF (basic fibroblast growth factor) show a stimulating activity on HTFs, no effect, positive or negative, has been observed when these cells are grown in the presence of cartilage permeate (1 Kg/2 L). No hypoplasiant effect could be observed. This suggests that the permeate has an hypoplasiant effect which is specific to tumor cells with no detectable effect on normal cells. The same cartilage extract neither had an effect on another type of fibroblast cells, HSF (Human Skin Fibroblasts; data not shown). Eventhough not tested, it is assumed that the lyophilizate also shows no effect on normal cells.

Clinical Trials

Before proceeding with preliminary clinical trials, the crude permeate obtained after ultrafiltration was 2 and 20 fold-concentrated, providing enriched active permeate. These levels of concentration were obtained on a tangential flow filtration column having a porosity of 1000 Daltons, which reduced the volume of the eluate by 2 and 20 times. The concentrated permeate was filtered of a millipore filter of a porosity of 0.22 μm. When the cartilage was processed with the alternative centrifuge method (using the CEPA centrifuge with a membrane of a porosity of 30 μM), a ten-fold concentration achieved the obtention of a concentrated extract having almost the same proteic level as the above 20-fold concentrated extract, e.g. 12 mg/mL (improved method) instead of 14 mg/mL (laboratory scale method). The sterile 10× concentrated permeate was distributed in 7 mL aliquotes (about 85 mg of proteins) in sterile flasks, frozen at −80° C. overnight and further stored at −20° C. until utilization. The major difference between the crude and the concentrated permeates is their concentration in proteins. It will be noted that the method used for determining the proteic content measures nitrogen compounds and not only proteins (Kjeldahl method). This may explain why the concentration of proteins does not increase proportionally with the level of volume concentration as this is usually the case when the proteic content is determined by the Lowry method. The concentration step is thus assumed to allow permeation of water as well as low molecular weight nitrogen compounds.

The concentrated permeate was used for treating angiogenesis-dependent diseases. Two different types representative of angiogenesis-dependent diseases were tested in practice in human; the first type being dermatological disorders (psoriasis) and the second type being cancer (prostate cancer).

Among dermatological diseases, psoriasis cases were selected. Among the psoriasis cases tested, it is worthwhile to note the difference between psoriasis cases complicated by hyperkeratosis and non-complicated ones. The keratosis component of this disease is not substantially affected per se by the concentrated cartilage permeate while, in contrast, the angiogenic component is the target of choice for this mixture of active ingredients. The examples below will illustrate and confirm this statement.

A patient suffering of a prostate cancer has voluntary tried a 10 fold-concentrated cartilage permeate. This patient underwent a series of successive conventional therapies that were temporarily successful. He recently began to consume the cartilage extract after his cancer showed recidivism.

The results shown hereinbelow are very encouraging and are deemed predictive of the usefulness of the crude permeate and fractions thereof in the treatment of all angiogenesis-dependent diseases, and not only to the ones specifically tested. Insofar as a disease has an angiogenic component, it is deemed that the cartilage extract of the present invention will be effective in this respect provided that it enters a composition containing an effective amount thereof and that this composition is in a suitable form for proper administration. Therefore, it will be appreciated that the present invention is not limited to the following specific compositions, since the person skilled in the art would be able to derive numerous compositions wherein choice is guided by the mode of administration thereof and the targeted ill tissue. Compositions may be administered by different routes e.g. topical, oral, sublingual, rectal, intravenous, intramuscular, by diffusion, etc.

Psoriasis

The following dermatological composition was made and tried to verify its efficacy in patients suffering of psoriasis:

EMULGADE™ (mixture of stearates, esters, fatty alcohols and nonionic emulsifiers) CLB 29% (W/W)

20X crude permeate 69.5% (W/W)

GERMABEN™ II (diazolidinyl urea, methylparaben, propylparaben and propylene glycol) 1% (W/W), and Lavandula Angustifolia 0.5% (W/W)

EMULGADE™ CLB, a mixture of stearate esters, fatty alcohols and nonionic emulsifiers (purchased from Henkel Canada Ltd.) was heated at 65–70° C. under agitation. Heating was stopped while the mixture was kept under agitation. When the mixture reached a temperature of 45° C., the essential oil Lavandula Augustifolia and the preservative agents GERMABEN™II (diazonidyl urea 30%, methylparaben 11, propylparaben 3% and propylene glycol 56%; purchased from Sutton Laboratories, N.J., U.S.A.) were added. When the temperature of the mixture reached 30° C., the cartilage extract was added. The composition so obtained was a smooth non-greasy cream; by varying the percentage of EMULGADE™, other forms of various viscosity dermatological compositions can be obtained, in accordance with the manufacturer's directives (milk, lotion, ointment). Other vehicles or excipient might be used to obtain pastes, gels and any other form of transdermal preparation.

The above formulation was given twice daily during a period of twelve weeks to a panel of ten patients (topical application) suffering of psoriasis that had been responsive to the conventional therapies tried but became refractory to them after a while. For this study, patients were selected for the similar and symmetrical extent of psoriasis on both side members. These trials were conducted in a double-blind fashion, neither the dermatologist nor the patients knowing which affected side was treated with the composition containing the cartilage extract and which one was treated with a control-composition. Remarkable improvement was observed in five patients whose psoriasis was not complicated by hyperkeratosis; photographs of parts of two patients' bodies are shown in FIGS. 9a), 9b), 10a) and 10b). In FIGS. 9a) and 9b), it is demonstrated that a patient affected by psoriasis with hyperkeratosis has nevertheless shown a very significant reduction of the erythema, associated with no prurit, after only one month of treatment. The hyperkeratosis remained, however, important. Photographs of the second patient suffering of psoriasis not complicated with hyperkeratosis (FIGS. 10a and 10b)) show a much better improvement after a three month-treatment. Since psoriasis appears to be a multifactorial disease, it is assumed that the response of the patients depends on the importance of the involvement of angiogenic factor in the establishment and in the perpetuation of this condition. It is probable that better results might be obtained if this kind of formulation is complemented with other therapeutic agents addressing to other factors involved (keratolytic agents, anti-inflammatory agents, antihistaminics, immunosuppressors, etc.).

This complementation may take the form of amending the formulation to include an effective amount of a keratolytic agent, for example. It could also be achieved by the separate administration of such a complementary therapeutic agent, concurrently or in alternation with the application of the present topical formulation. Furthermore, the complementary medication does not need to be administered by the same route.

The above formulation has shown no systemic effect (the effect being limited to the treated member) and no secondary effect despite the high proportions in cartilage extract.

Acne

Even though acne is not to the inventors' knowledge, classified as a disease or disorder having an angiogenic component, it was nevertheless tempting to test the liquid cartilage extract in patients so affected. For experimenting the cartilage extract in patients affected by acne, the following gel formulation was made:

CARBOPOL™ (carboxypolymethylene) 1.2%

Purified water 77.2%

NaOH 0.3%

PHENOXETOL™ (2-phenoxyethanol) 0.3%

Tween 80™ 0.3%

2× cartilage extract 20.0%

40× Aloes extract 0.5%

The 2× cartilage extract contains 9–12 mg/mL of proteins. This formulation shows a remarkable improvement of the aspect of the skin of patients affected by more or less severe forms of acne (inflammatory acnae and kystic acne; data not shown).

These surprising results may be due to an anti-angiogenic effect (thus revealing an angiogenic component in acne), or they may be due to active ingredients that have an effect other than anti-angiogenic. It is recalled here that the same extract has at least one other effect than an anti-angiogenic effect: a direct hypoplasiant effect has demonstrated in cancer cell lines.

Cancer

One patient suffering of prostate cancer has tried the 10 fold-concentrated permeate. An adenocarcinoma was diagnosed in 1986. At that time, radiotherapy was undertaken. In 1991, the PSA (Prostatic serum antigen) level was 138 µg/L, when the normal acceptable higher limit is 4 µg/L. The patient then underwent a completely different therapy by castration combined with anti-androgen therapy (EUFLEX™(Flutamide)). This treatment was efficient during three years, after which PSA level began to rise again. Since June 1994, this patient consumes the 10× permeate (daily sublingual dose of about 75 mg of proteins/7 mL of distilled water, equivalent to about 1–1.5 mg/kg of body weight/day). Even though a significant amount of this dose is swallowed, it is probably absorbed in the gastro-intestinal tract, if the results obtained in DMBA-treated animals (see above) are relied upon. The PSA levels decreased from 12 to 0.9 µg/mL (last results obtained in December 1994). This dose regimen can also be modified at will in accordance with the route of administration, the bioavailability of the active ingredients and the desired aggressiveness with which the pathology is to be controlled. At this time, the non-toxicity has been verified in rats (see above-examples) and in humans (data not shown).

In the other in vivo experiment performed on DMBA-treated rats, the dosage rate of the liquid extract was about 190–220 mg of proteins/Kg of body weight, which presumably had a great contribution to the reduction of the area of cancer blood vessels (55% when combined with a much larger dose of lyophilizate). It is therefore assumed that a dose of about 1 to about 200 mg/Kg of body weight per day is a reasonable range of median doses ($ED_{50}$) for treating cancer by reducing or abolishing angiogenesis.

These results show the great potential of the cartilage liquid extract in the treatment of angiogenesis-dependent diseases. The amount of cartilage extract as well as the formulation thereof may be varied at will to fulfil specific needs. It is assumed that fractions of the crude permeate which contain the active ingredient will also be effective. These fractions await further characterization.

One can note that, on a proteic content basis, the topical formulations for the skin may contain a wide range of doses of the cartilage extract. In the two specific categories of cases tested, for example, the ratio of the final protein concentration in the formulations for treating psoriasis versus acne is 4–5, while the ratio of dilution of the permeate is 35. For all predicted applications in angiogenesis-dependent diseases (from ophthalmic drops to dermatological and cancer drug formulations), it is presumed that a minimal final protein concentration of the crude permeate could be very low (less than 0.1 mg/mL). This lower range of doses depends on the accessibility and on the permeation of the active ingredients to the site of action as well as on the efficient capture of these ingredients and the sensitivity or response of the tissue to angiogenic inhibitors. The higher limit of the final protein concentration in formulations for some applications is not currently known. The highest final concentrations tried were of about 9 mg/mL of proteins in the formulation for the psoriasis cases and about 12 mg/mL in the dose unit of 7 mL administered in the prostate cancer case. Since the crude permeate cannot be lyophilized without losing its activity, it is deemed that the highest doses depend on the limit of concentration that one can practice on the crude permeate e.g. till the obtention of a concentrated syrup.

Required Material

Coolers

Surgical instruments

Meat chopper

Plastic bags

Industrial blender (Waring 3-speed blender bought from Fisher Scientific)

A system of purification of water (inverse osmosis and 0.1 µm filtration; Continental Water System, model PRE 2202, serial number 91089, Modulab Bioscience RQ/Polishing System bought from Fisher Scientific, Montreal, Quebec). This system provides an apyrogenic water of high quality.

A precision balance Mettler, series AE bought from Fisher Scientific

Centrifuge Sorvall RC-285 bought from DuPont Canada

Centrifuge CEPA

Nylon pocket of a porosity of 30 µM

An autoclave (automatic vapor sterilizer Sanyo, model MAC 350P)

Nalgene 500 mL containers sterilized at 132° C. for 10 minutes and dried for 35 minutes Conical filters of 24 µm porosity Whatman Reeve Angel Ultrafiltration column (Molecular weight cut-off: 500 KDaltons and (1 KD when applicable); Surface: 25 square feet; Flow: 130 L/minute; Inlet pressure: 30 psi; Outlet pressure: 5 psi; bought from Koch Membrane Systems Inc., Wilmington, Mass., USA)

Sanitary centrifuge pump (Monarch Industries, model ACE-S100, type A) for providing a 130 L/minute flow sterile hut (laminar flow hut NuAire bought from Ingram & Bell)

Millipack-60 0.22 µm sterile filters

Sterile clear or amber glass bottles

Concentrator DC-10 Amicon

Rotofor Biorad 170-2950

Amicon filters SIOY10, SIOY30 and SIOY100 of cut-off values of 10, 30 and 100 KD, respectively FPLC Pharmacia 216007 (computer Pharmacia 216014)

SEPHACRYL S-300™ (cross-linked co-polymer of allyl dextran and N,N methylene bisacrylamide) 26 mm/60 cm (Pharmacia)

SUPEROSE S-12™ (cross-linked agarose) 10 mm/30 cm (Pharmacia)

Lyophilizer Labconco 10273 A

This invention has been described hereinabove, and it should be appreciated that it would be well within the ability and the knowledge of the person skilled in the art, without departing from the teachings of this disclosure, to bring modifications by replacing some elements of this invention as practicized by their equivalents, which would achieve the same goal thereof. These obvious variations are deemed covered by this application.

What is claimed is:

1. A cartilage extract produced by a method which comprises the following steps:
   a) homogenizing pieces of shark cartilage in an aqueous solution which is non-denaturing towards biological active components until said pieces of shark cartilage are reduced to solid particles whose size is lower than or equal to about 500 um;
   b) extracting biologically active components into said aqueous solution, which results in a mixture of said solid particles and a crude liquid extract;
   c) separating said crude liquid extract from said solid particles; and
   d) fractionating the crude liquid extract so as to obtain a final liquid extract containing molecules having a molecular weight lower than about 500 KDa.

2. A liquid fraction of the final liquid extract of claim 1 which comprises molecules having a molecular weight of about 1 to about 2.5 KDa measured by Fast protein liquid chromatography (FPLC).

3. A liquid fraction of the final liquid extract of claim 1 which comprises molecules having a molecular weight of about 29 KDa and an isoelectric point of about 5.3 to about 6.26, measured by electrophoresis or Fast protein liquid chromatography (FPLC) after a Rotofor separation.

4. A liquid fraction of the final liquid extract of claim 1 which comprises molecules having a molecular weight of about 35 KDa and an isoelectric point of about 7.64 to about 7.94, measured by electrophoresis after a Rotofor separation.

5. A liquid fraction of the final liquid extract of claim 1 which comprises molecules having a molecular weight of about 48 KDa and an isoelectric point of about 7.29 to about 7.94, measured by electrophoresis after a Rotofor separation.

6. A liquid fraction of the final liquid extract of claim 1 which comprises molecules having a molecular weight of about 60 KDa and an isoelectric point of about 5.30 to about 6.26, measured by electrophoresis after a Rotofor separation.

7. A liquid fraction of the final liquid extract of claim 1 which comprises molecules having a molecular weight of about 70 to about 120 KDa measured by Fast protein liquid chromatography after a Rotofor separation.

8. A liquid fraction of the final liquid extract of claim 1 which comprises molecules having a molecular weight of about 60 to about 70 KDa measured by Fast protein liquid chromatography after a Rotofor separation.

9. A liquid fraction of the final liquid extract of claim 1 which comprises molecules having a molecular weight of about 35 to about 46 KDa measured by Fast protein liquid chromatography after a Rotofor separation.

10. A composition for treating dermatological disorders or diseases having one or more etiological components selected from the group consisting of tumor proliferation and angiogenesis, said composition comprising a therapeutically effective amount of a cartilage extract as recited in claim 1 in adjunction with a pharmaceutically suitable vehicle.

11. A composition for treating cancer which comprises a therapeutically effective amount of a cartilage extract as recited in claim 1 in adjunction with a pharmaceutically suitable vehicle.

12. A composition for treating diseases or disorders having one or more etiological components selected from the group consisting of tumor proliferation and angiogenesis, said composition comprising an effective amount of a cartilage extract as recited in claim 1 and a pharmaceutically acceptable vehicle.

13. A method for treating diseases or disorders having one or more etiological components selected from the group consisting of tumor proliferation and angiogenesis, said method comprising the step of administering to a patient in need of such a treatment an effective amount of a cartilage extract as recited in claim 11.

14. The extract of claim 1, wherein said aqueous solution is purified water.

15. The extract of claim 1, wherein shark cartilage is present in proportions of 1 Kg in 1 liter or more aqueous solution volume.

16. A cartilage extract produced by a method which comprises the following steps performed at about 4° C.:
   a) homogenizing pieces of shark cartilage in an aqueous solution which is non-denaturing towards biological active components until said pieces of shark cartilage are reduced to solid particles whose size is lower than or equal to about 500 μm;
   b) extracting biologically active components into said aqueous solution, which results in a mixture of said solid particles and a crude liquid extract;
   c) separating said crude liquid extract from said solid particles; and
   d) fractionating the crude liquid extract so as to obtain a final liquid extract containing molecules having a molecular weight lower than about 500 KDa.

17. A composition for treating dermatological disorders or diseases having one or more etiological components selected from the group consisting of tumor proliferation and angiogenesis, said composition comprising a therapeutically effective amount of a cartilage extract as recited in claim 16 in adjunction with a pharmaceutically suitable vehicle.

18. A composition for treating diseases or disorders having one or more etiological components selected from the group consisting of tumor proliferation and angiogenesis, said composition comprising an effective amount of a cartilage extract as recited in claim 16 and a pharmaceutically acceptable vehicle.

19. A method for treating diseases or disorders having one or more etiological components selected from the group consisting of tumor proliferation and angiogenesis, said method comprising the step of administering to a patient in need of such a treatment an effective amount of a cartilage extract as recited in claim 16.

20. The extract of claim 16, wherein said aqueous solution is purified water.

21. The extract of claim 16, wherein shark cartilage is present in proportions of 1 Kg in 1 liter or more aqueous solution volume.

22. A composition for treating cancer which comprises a therapeutically effective amount of a cartilage extract as recited in claim 16 in adjunction with a pharmaceutically suitable vehicle.

23. A composition as recited in claim 22, wherein said cartilage extract has an equivalent of about 75 mg (dry weight) in 7 ml of water as a carrier.

24. A composition for as recited in claim 23 which is a composition to be administered sublingually to a patient in need of such a treatment.

25. A cartilage extract produced by a method which comprises the following steps:
   a) homogenizing pieces of shark cartilage in an aqueous solution which is non-denaturing towards biological active components until said pieces of shark cartilage are reduced to solid particles whose size is lower than or equal to about 500 um;

b) extracting biologically active components into said aqueous solution, which results in a mixture of said solid particles and a crude liquid extract;

c) separating said crude liquid extract from said solid particles;

d) fractionating the crude liquid extract so as to obtain a final liquid extract containing molecules having a molecular weight lower than about 500 KDa; and e) concentrating said final liquid extract on a membrane having a nominal molecular weight cut-off value of about 1 KDa, resulting in a concentrated liquid extract comprising molecules of a molecular weight lower than about 500 KDa which is enriched in molecules having a molecular weight comprised between about 1 KDa to about 500 KDa.

26. A topical composition for treating psoriasis comprising an equivalent of about 10 mg (dry weight) of the cartilage extract of claim 25 per ml of composition as a therapeutically effective ingredient in adjunction with a pharmaceutically suitable vehicle.

27. A topical composition for treating acne comprising an equivalent of about 2 mg (dry weight) of the cartilage extract of claim 25 per ml of composition as a therapeutically effective ingredient in adjunction with a pharmaceutically suitable vehicle.

28. A composition for treating cancer which comprises a therapeutically effective amount of a cartilage extract as recited in claim 25 in adjunction with a pharmaceutically suitable vehicle.

29. A composition for treating diseases or disorders having one or more etiological components selected from the group consisting of tumor proliferation and angiogenesis, said composition comprising an effective amount of a cartilage extract as recited in claim 25 and a pharmaceutically acceptable vehicle.

30. A method for treating diseases or disorders having one or more etiological components selected from the group consisting of tumor proliferation and angiogenesis, said method comprising the step of administering to a patient in need of such a treatment an effective amount of a cartilage extract as recited in claim 25.

31. The extract of claim 25, wherein said aqueous solution is purified water.

32. The extract of claim 25, wherein shark cartilage is present in proportions of 1 Kg in 1 liter or more aqueous solution volume.

33. A composition for treating dermatological disorders or diseases having one or more etiological components selected from the group consisting of tumor proliferation and angiogenesis, said composition comprising a therapeutically effective amount of a cartilage extract as recited in claim 25 in adjunction with a pharmaceutically suitable vehicle.

34. A composition as recited in claim 33, wherein said cartilage extract is added to achieve a final cartilage dry weight amount of about 2 to about 10 mg per ml of composition.

35. The cartilage extract of claim 25 wherein steps a) to e) are performed at about 4° C.

36. A composition for treating dermatological disorders or diseases having one or more etiological components selected from the group consisting of tumor proliferation and angiogenisis, said composition comprising a therapeutically effective amount of cartilage extract as recited in claim 35 in adjunction with a pharmaceutically suitable vehicle.

37. A topical composition for treating psoriasis comprising an equivalent of about 10 mg (dry weight) of the cartilage extract of claim 35 per ml of composition as a therapeutically effective ingredient, in adjunction with a pharmaceutically suitable vehicle.

38. A topical composition for treating acne comprising an equivalent of about 2 mg (dry weight) of the cartilage extract of claim 35 per ml of composition, as a therapeutically effective ingredient in adjunction with a pharmaceutically suitable vehicle.

39. A composition for treating cancer which comprises a therapeutically effective amount of a cartilage extract as recited in claim 35 in adjunction with a pharmaceutically suitable vehicle.

40. A composition for treating diseases or disorders having one or more etiological components selected from the group consisting of tumor proliferation and angiogenesis, said composition comprising an effective amount of a cartilage extract as recited in claim 35 and a pharmaceutically acceptable vehicle.

41. A method for treating diseases or disorders having one or more etiological components selected from the group consisting of tumor proliferation and angiogenesis, said method comprising the step of administering to a patient in need of such a treatment an effective amount of a cartilage extract as recited in claim 35.

42. The extract of claim 35, wherein said aqueous solution is purified water.

43. The extract of claim 35, wherein shark cartilage is present in proportions of 1 Kg in 1 liter or more aqueous solution volume.

44. A cartilage extract produced by a method which comprises the following steps:

a) homogenizing pieces of shark cartilage in an aqueous solution which is non-denaturing towards biological active components until said pieces of shark cartilage are reduced to solid particles whose size is lower than or equal to about 500 um;

b) extracting biologically active components into said aqueous solution, which results in a mixture of said solid particles and a crude liquid extract;

c) separating said crude liquid extract from said solid particles;

d) fractionating the crude liquid extract so as to obtain a final liquid extract containing molecules having a molecular weight lower than about 500 KDa; and e) fractionating said final liquid extract, to obtain a liquid sub-fraction of said liquid extract.

45. The extract of claim 44, wherein said aqueous solution is purified water.

46. The extract of claim 44, wherein shark cartilage is present in proportions of 1 Kg in 1 liter or more aqueous solution volume.

47. A composition for treating diseases or disorders having one or more etiological components selected from the group consisting of tumor proliferation and angiogenesis, said composition comprising an effective amount of a cartilage extract as recited in claims 1, or 16, or 25, or 44 and a pharmaceutically acceptable vehicle.

48. A method for treating diseases or disorders having one or more etiological components selected from the group consisting of tumor proliferation and angiogenesis, said method comprising the step of administering to a patient in need of such a treatment an effective amount of a cartilage extract as recited in claims 1, or 16, or 25, or 44.

49. A cartilage extract produced by a method which comprises the following steps:

a) homogenizing pieces of shark cartilage in an aqueous solution which is non-denaturing towards biological active components, until said pieces of shark cartilage are reduced to solid particles whose size is lower than or equal to about 500 μm;

b) extracting biologically active components into said aqueous solution, which results in a mixture of said solid particles and a crude liquid cartilage;

c) separating said crude liquid extract from said solid particles;

d) fractionating said crude liquid extract so as to obtain a sub-fraction of said crude liquid extract, said sub-fraction containing molecules having a molecular weight lower than about 500 KDa; and e) further fractionating said sub-fraction of said crude liquid extract on a membrane having a nominal molecular weight cut-off value of about 1 KDa, to form a final liquid extract comprising molecules of a molecular weight lower than about 1 KDa.

50. A composition comprising a liquid extract as defined in claim 49 and an acceptable pharmaceutical vehicle.

51. A shark cartilage extract comprising at least one biologically active component having a molecular weight of less than about 500 KDa; an anti-angiogenic activity; an in vitro anti-tumor activity as determined by an anti-tumor activity assay where angiogenesis does not play a role in cell proliferation; and an in vivo anti-tumor activity in tumors where angiogenesis plays a role in cell proliferation; wherein said in vivo anti-tumor activity can be independent of anti-angiogenic activity.

52. A shark cartilage extract according to claim 51, wherein said at least one biologically active component has a molecular weight in the range of about 1 to about 500 KDa.

53. A shark cartilage extract according to claim 51, wherein said at least one biologically active component comprises at least one biologically active component having one of the following:

a molecular weight in the range of about 1 to about 2.5 KDa;

a molecular weight in the range of about 29 KDa;

a molecular weight in the range of about 35 KDa;

a molecular weight in the range of about 35 to about 46 KDa;

a molecular weight in the range of about 48 KDa;

a molecular weight in the range of about 60 KDa;

a molecular weight in the range of about 60 to about 70 KDa; and a molecular weight in the range of about 70 to about 120 KDa.

54. A shark cartilage extract according to claim 51, wherein said at least at one biologically active component comprises at least one biologically active component having one of the following properties:

an isoelectric point of about 5.3 to about 6.26;

an isoelectric point of about 7.64 to about 7.94; and an isoelectric point of about 7.29 to about 7.94.

55. A pharmaceutical composition comprising a shark cartilage extract as defined in claim 51.

56. A method of treating diseases or disorders selected from the group consisting of tumor proliferation and angiogenesis, said method comprising the step of administering to a patient in need of such treatment an effective amount of a shark cartilage extract as defined in claim 51 for a period of time to sufficient treat said diseases or disorders.

57. A method according to claim 56, wherein said diseases or disorders are selected from the group consisting of acme, psoriasis, and cancer.

* * * * *

UNITED STATES PATENT AND TRADEMARK OFFICE
CERTIFICATE OF CORRECTION

PATENT NO. : 5,985,839
DATED : November 16, 1999
INVENTOR(S) : Eric Dupont, Paul Brazeau and Christina Juneau It is certified that error appears in the above-identified patent and that said Letters Patent is hereby corrected as shown below:

Title page,
Item [75], Inventors, replace "Christian Juneau" with -- Christina Juneau --
Item [73], Assignee, replace "Les Laboratories Aeterna Inc." with
-- Les Laboratoires Aeterna Inc. --

Signed and Sealed this

Twelfth Day of August, 2003

JAMES E. ROGAN
*Director of the United States Patent and Trademark Office*